United States Patent
Inamoto et al.

(10) Patent No.: US 11,543,389 B2
(45) Date of Patent: Jan. 3, 2023

(54) VIBRATIONAL SENSING SYSTEM, VIBRATIONAL SENSING METHOD, AND NON-TRANSITORY COMPUTER READABLE MEDIUM FOR SENSING GROWTH DEGREE OF FRUIT CROP

(71) Applicants: MITSUMI ELECTRIC CO., LTD., Tama (JP); YANMAR POWER TECHNOLOGY CO., LTD., Osaka (JP)

(72) Inventors: Shigenori Inamoto, Tama (JP); Takanori Hanayama, Tama (JP); Akio Ishii, Osaka (JP); Toru Takemoto, Osaka (JP)

(73) Assignees: MITSUMI ELECTRIC CO., LTD., Tokyo (JP); YANMAR POWER TECHNOLOGY CO., LTD., Osaka (JP)

( * ) Notice: Subject to any disclaimer, the term of this patent is extended or adjusted under 35 U.S.C. 154(b) by 90 days.

(21) Appl. No.: 16/978,632

(22) PCT Filed: Mar. 11, 2019

(86) PCT No.: PCT/JP2019/009812
§ 371 (c)(1),
(2) Date: Sep. 4, 2020

(87) PCT Pub. No.: WO2019/176882
PCT Pub. Date: Sep. 19, 2019

(65) Prior Publication Data
US 2020/0408719 A1  Dec. 31, 2020

(30) Foreign Application Priority Data
Mar. 16, 2018 (JP) .............................. JP2018-049513

(51) Int. Cl.
*G01N 29/12* (2006.01)
*A01G 7/00* (2006.01)
(Continued)

(52) U.S. Cl.
CPC ............... *G01N 29/12* (2013.01); *A01G 7/00* (2013.01); *G01B 17/00* (2013.01); *G01N 29/4427* (2013.01); *G01N 33/025* (2013.01)

(58) Field of Classification Search
CPC .. G01N 29/12; G01N 29/4427; G01N 33/025; A01G 7/00; G01B 17/00
(Continued)

(56) References Cited

U.S. PATENT DOCUMENTS 5,152,401 A  * 10/1992 Affeldt, Jr. .......... G01N 29/4445
                                                                    209/931
6,276,536 B1 *  8/2001 Terasaki ................. G01N 29/12
                                                                    702/56
(Continued)

FOREIGN PATENT DOCUMENTS

CN 107634676 A  * 1/2018
CN 113711773 A  * 5/2021
(Continued)

OTHER PUBLICATIONS

Translation FR-2762094 (Year: 1998).*
(Continued)

*Primary Examiner* — Alexander A Mercado
*Assistant Examiner* — Monica S Young
(74) *Attorney, Agent, or Firm* — McCoy Russell LLP

(57) ABSTRACT

A sensing system contains a vibration device attached to a stem of an agricultural crop for applying vibration to the agricultural crop, at least one sensor attached to the stem of the agricultural crop for sensing vibration of the agricultural crop caused by the vibration applied to the agricultural
(Continued)

product from the vibration device to transmit vibration information relate to the vibration of the agricultural crop and a computing device for identifying one local maximum value among a plurality of local maximum values in a frequency spectrum obtained from the vibration information received from the at least one sensor as a resonance frequency of the vibration of the agricultural crop to determine a growth degree of a fruit of the agricultural crop based on the identified resonance frequency.

13 Claims, 10 Drawing Sheets

(51) Int. Cl.
   *G01B 17/00* (2006.01)
   *G01N 29/44* (2006.01)
   *G01N 33/02* (2006.01)
   *A01G 7/06* (2006.01)

(58) Field of Classification Search
   USPC .......................................................... 73/579
   See application file for complete search history.

(56) References Cited

U.S. PATENT DOCUMENTS

| | | | | |
|---|---|---|---|---|
| 9,532,508 | B1* | 1/2017 | Stubbs | G06V 10/10 |
| 2006/0288784 | A1* | 12/2006 | Huang | G01N 29/07 |
| | | | | 73/597 |
| 2007/0079644 | A1* | 4/2007 | Clark | G01N 29/42 |
| | | | | 73/12.01 |
| 2011/0040504 | A1* | 2/2011 | Liu | G01N 33/025 |
| | | | | 702/56 |
| 2011/0288689 | A1* | 11/2011 | Kageyama | G01N 29/07 |
| | | | | 73/599 |
| 2016/0309659 | A1* | 10/2016 | Guy | A01G 25/16 |
| 2018/0275108 | A1* | 9/2018 | Cocker | G01N 29/348 |
| 2020/0292514 | A1* | 9/2020 | Azuma | A01G 7/00 |
| 2022/0120716 | A1* | 4/2022 | Irie | G01M 5/0033 |

FOREIGN PATENT DOCUMENTS

| | | | | | |
|---|---|---|---|---|---|
| FR | 2762094 | A1 * | 10/1998 | | G01G 3/16 |
| FR | 2762094 | A1 | 10/1998 | | |
| JP | H09236587 | A * | 9/1997 | | |
| JP | 2003509023 | A * | 9/2000 | | |
| JP | 2003083952 | A * | 3/2003 | | |
| JP | 2004101452 | A | 4/2004 | | |
| JP | 2015112083 | A | 6/2015 | | |
| JP | 2017136041 | A | 8/2017 | | |
| JP | 2019033672 | A | 3/2019 | | |
| RU | 2636955 | C2 * | 11/2017 | | A01G 7/04 |
| WO | WO-2012067485 | A1 * | 5/2012 | | G01N 21/84 |
| WO | WO-2013181558 | A1 * | 12/2013 | | G01B 5/0035 |
| WO | WO-2015092799 | A1 * | 6/2015 | | A01G 22/00 |
| WO | 2019031181 | A1 | 2/2019 | | |
| WO | WO-2022055353 | A1 * | 3/2022 | | |

OTHER PUBLICATIONS

Translation JP-H09236587-A (Year: 1997).*
European Patent Office, Extended European Search Report Issued in Application No. 19766629.0, dated Oct. 18, 2021, Germany, 8 pages.
ISA Japanese Patent Office, International Search Report Issued in Application No. PCT/JP2019/009812, dated Jun. 11, 2019, WIPO, 2 pages.

* cited by examiner

VIBRATIONAL SENSING SYSTEM, VIBRATIONAL SENSING METHOD, AND NON-TRANSITORY COMPUTER READABLE MEDIUM FOR SENSING GROWTH DEGREE OF FRUIT CROP

CROSS-REFERENCE TO RELATED APPLICATIONS

The present application is a U.S. National Phase of International Patent Application Serial No. PCT/JP2019/009812 entitled "SENSING SYSTEM, SENSING METHOD, AND NON-TRANSITORY COMPUTER-READABLE MEDIUM," filed on Mar. 11, 2019. International Patent Application Serial No. PCT/JP2019/009812 claims priority to Japanese Patent Application No. 2018-049513 filed on Mar. 16, 2018. The entire contents of each of the above-referenced applications are hereby incorporated by reference for all purposes.

TECHNICAL FIELD

The present invention generally relates to sensing systems, sensing methods and non-transitory computer readable media for sensing a growth degree of a fruit of an agricultural crop, in particular to a sensing system, a sensing method and a non-transitory computer readable medium for applying vibration to the agricultural crop, identifying one local maximum value among a plurality of local maximum values in a frequency spectrum obtained from vibration information related to vibration of the agricultural crop caused by the applied vibration as a resonance frequency of the vibration of the agricultural crop and sensing the growth degree of the fruit of the agricultural crop based on the identified resonance frequency.

BACKGROUND AND SUMMARY

BACKGROUND ART

In recent years, needs of improving efficiency in the agriculture field and adding a higher value to an agricultural crop have increased due to some factors such as intensification of international competition in an agriculture field caused by promotion of international free trade policies, sluggish prices of agricultural crops and rising prices of production materials. In order to improve the efficiency in the agriculture field and add the higher value to the agricultural crop, it is very important that an agricultural operator accurately predicts a schedule indicating when and how many agricultural crops will be harvested and shipped.

Such a schedule is essential information when the agricultural operator develops his/her business plans. If accuracy of this information is low, the agricultural operation cannot help but develop ambiguous business plans. One of the biggest concerns of the agricultural operator is that it is difficult to pass a financing examination of a financial organization such as a bank even if the agricultural operator applies a financial loan of the financial organization for his/her agricultural business because the agricultural operator cannot help but develop the ambiguous business plans. Thus, it is virtually impossible to receive the financial loan from the financial organization such as the bank. This situation hampers motivated agricultural operators who want to perform large-scale investments to make agriculture more efficient and value-added. In Japan, Japan Agricultural Cooperative Association (JA) has been responding to such loan needs from the agricultural operators. However, there are needs of the agricultural operators to receive more financial loans from not only Japan Agricultural Cooperative Association but also other financial organizations. For this reason, there are great needs to accurately sense a growth degree of the agricultural crop and obtain an accurate schedule for agricultural crop harvesting and shipping in order to develop accurate business plans.

In recent years, it is widely performed that an agricultural operator has entered into direct contracts with retail stores such as supermarkets and vegetable shops or eating houses such as restaurants and pubs to directly sell his/her agricultural crop. By concluding such a direct contract between the agricultural operator and the retail stores or the eating houses, it becomes possible to sell the agricultural crop with a relatively high price compared with the case where the agricultural crop is sold to the retail stores or the eating houses through a middleman such as Japan Agricultural Cooperative Association because the agricultural operator can guarantee safety and taste of the agricultural crop to users. However, it is impossible to accurately predict the schedule indicating when and how much agricultural crops can be harvested and shipped in the present situation as described above. Thus, when the agricultural operator concludes the direct contract with the retail stores or the eating houses, the agricultural operation often declares a relatively-small number of agricultural crops which are expected to be delivered by the time of delivery. This declaration is performed for preventing the contract from being violated if the number of agricultural crops which can be delivered does not reach the contracted number due to some factors such as bad weather. However, in the case where the small number of agricultural crops is declared as described above, there is a problem that some of the agricultural crops are wasted by a number exceeding the contracted number when a large number of agricultural crops are harvested. In order to avoid such a problem, there are the great needs to accurately sense the growth degree of the agricultural crop to obtain the accurate schedule for the agricultural crop harvesting and shipping.

Further, in China and the United States, it is widely performed that agricultural operators have entered into direct contracts with users who are end consumers to sell a high value-added agricultural crop to the users without through agricultural associations or retail stores. This is a selling model based on urgent needs to check food safety in China. On the other hand, this is a selling model based on needs for a high value-added agricultural crop (e.g., an organic vegetable) for a wealthy class in the United States. When the agricultural operator directly sells the agricultural crop to the users as described above, there are needs to provide the users with information related to the growth degree of the agricultural crop in real time via the Internet or the like for increasing a degree of satisfaction of the users. By increasing the satisfaction of the users, it becomes possible to sell the agricultural crop with a higher price. For this reason, there are the great need to accurately sense the growth degree of the agricultural crop.

Further, in general, when fruit vegetables such as tomatoes and eggplants and fruit-like vegetables such as strawberries are sold to the retail stores through the middleman such as the agricultural association, a time duration from when fruits are harvested to when users who are end consumer purchase is relatively long. Thus, the agricultural operator harvests and ships the fruit of the agricultural crop before the fruit gets fully ripe (for example, in the case of tomato, the fruit is in a blue state) so that the fruit of the agricultural crop appears to be most palatable (for example, in the case of tomato, the fruit is in a most-red state) when the fruit of the agricultural crop is lined up in the retail store. On the other hand, in the case of directly selling the agricultural crop to the users as described above, it is possible to secure a long time for maturing the agricultural crop since the time from when the agricultural crop is harvested to when the agricultural crop is delivered to the users who are the end consumers is short. In this case, it is important to know information indicating which fruit has ripened fully and when and which fruit will ripen fully. In order to know such information, there are the great needs to accurately sense the growth degree of the agricultural crop.

As a sensing system related to the agricultural crop, there is known a system for sensing a growth environment for the agricultural crop (temperature, humidity and the like in a vinyl house) as disclosed in patent document 1, for example. However, such a sensing system is intended to sense and control the growth environment for the agricultural crop and does not sense the growth degree of the agricultural crop. Thus, the sensing system does not match with the great needs described above.

In order to quantitatively determine the growth degree of the fruit of the agricultural crop such as the fruit vegetable (for example, tomato and eggplant) and the fruit-like vegetable (for example, strawberry), it is generally considered to measure a weight (mass) of the fruit of the agricultural crop by holding the fruit of the agricultural crop with a hand. However, when the weight of the fruit of the agricultural crop is measured, it is required to bring a measuring instrument such as a scale into contact with the fruit of the agricultural crop. Thus, there is a risk that the fruit of the agricultural crop is damaged due to the contact with the measuring instrument. Further, the measurement of the weight of the fruit of the agricultural crop is likely to be affected by disturbances such as wind and rain blowing against the fruit. Thus, it is often impossible to accurately determine the growth degree of the fruit of the agricultural crop. Furthermore, since such a work is performed manually by the agricultural operator one by one, a great burden is imposed on the agricultural operator.

RELATED ART DOCUMENT

Patent Document

JP 2017-136041A

Problems to be Solved by the Invention

The present invention has been made in view of the above-mentioned problems in the prior art. Accordingly, it is an object of the present invention is to provide a sensing system, a sensing method and a non-transitory computer readable medium for applying vibration to an agricultural crop, identifying one local maximum value among a plurality of local maximum values in a frequency spectrum obtained from vibration information related to vibration of the agricultural crop caused by the applied vibration as a resonance frequency of the vibration of the agricultural crop and sensing a growth degree of a fruit of the agricultural crop based on the identified resonance frequency.

Means for Solving the Problems

The above object is achieved by the present inventions defined in the following (1) to (9).

(1) A sensing system for sensing a growth degree of a fruit of an agricultural crop, comprising:

at least one vibration device attached to a stem of the agricultural crop for applying vibration to the agricultural crop;

at least one sensor attached to the stem of the agricultural crop for sensing vibration of the agricultural crop caused by the vibration applied to the agricultural crop from the vibration device to transmit vibration information related to the vibration of the agricultural crop; and a computing device for identifying one local maximum value among a plurality of local maximum values in a frequency spectrum obtained from the vibration information received from the at least one sensor as a resonance frequency of the vibration of the agricultural crop to determine the growth degree of the fruit of the agricultural crop based on the identified resonance frequency.

(2) The sensing system according to the above (1), wherein determination for growth of the fruit of the agricultural crop contains determination for a harvest time for the fruit of the agricultural crop.

(3) The sensing system according to the above (1) or (2), wherein the computing device determines that the fruit of the agricultural crop has grown to a size to be harvested when the identified resonance frequency is equal to or less than a predetermined threshold value.

(4) The sensing system according to any one of the above (1) to (3), wherein the sensing system uses the vibration device, the sensor and the computing device to identify the resonance frequency of the vibration of the agricultural crop at a predetermined cycle, and wherein the computing device compares the resonance frequency of the vibration of the agricultural crop identified from the vibration information obtained in a previous measurement with the resonance frequency of the vibration of the agricultural crop identified from the vibration information obtained in a current measurement and determines that a problem has occurred in growth of the fruit of the agricultural crop when the resonance frequency of the vibration of the agricultural crop does not shift to a low frequency side by a predetermined value or more.

(5) The sensing system according to any one of the above (1) to (4), wherein the computing device transmits determination for the growth of the agricultural crop to a user device.

(6) The sensing system according to any one of the above (1) to (5), wherein the fruit of the agricultural crop fruits at a point located between a point of the stem of the agricultural crop to which the at least one sensor is attached and a point to which the at least one vibration device is attached.

(7) The sensing system according to any one of the above (1) to (6), wherein the agricultural crop is a fruit vegetable or a fruit-like vegetable cultivated by a training method.

(8) A sensing method performed by a sensing system containing a computing device including a processor for sensing a growth degree of a fruit of an agricultural crop, comprising:

transmitting, by the processor, drive signals to at least one vibration device and at least one sensor each attached to a stem of the agricultural crop for driving the at least one vibration device to apply vibration to the agricultural crop and driving the at least one sensor to sense vibration of the agricultural crop caused by the vibration applied to the agricultural crop from the at least one vibration device;

receiving, by the processor, vibration information related to the vibration of the agricultural crop from the at least one sensor;

identifying, by the processor, one local maximum value among a plurality of local maximum values in a frequency spectrum obtained from the vibration information received from the at least one sensor as a resonance frequency of the vibration of the agricultural crop; and determining, by the processor, the growth degree of the fruit of the agricultural crop based on the identified resonance frequency.

(9) A non-transitory computer readable medium storing computer readable instructions executed by a computing device including a processor for sensing a growth degree of a fruit of an agricultural crop, wherein the computer readable instructions comprise:

an instruction for transmitting drive signals to at least one vibration device and at least one sensor each attached to a stem of the agricultural crop for driving the at least one vibration device to apply vibration to the agricultural crop and driving the at least one sensor to sense vibration of the agricultural crop caused by the vibration applied to the agricultural crop from the at least one vibration device;

an instruction for receiving vibration information related to the vibration of the agricultural crop from the at least one sensor;

an instruction for identifying one local maximum value among a plurality of local maximum values in a frequency spectrum obtained from the vibration information received from the at least one sensor as a resonance frequency of the vibration of the agricultural crop; and an instruction for determining the growth degree of the fruit of the agricultural crop based on the identified resonance frequency.

Effect of the Invention

The present invention uses the vibration device to apply the vibration to the agricultural crop, identifies one local maximum value among the plurality of local maximum values in the frequency spectrum obtained from the vibration information related to the vibration of the agricultural crop caused by the applied vibration and senses the growth degree of the fruit of the agricultural crop based on the identified resonance frequency. When the agricultural crop is vibrated, the vibrating agricultural crop can be considered as a resonant system defined by a spring constant of the stem of the agricultural crop and masses of the agricultural crop, the vibration device and the sensor. A resonance frequency of such a resonance system is not affected by disturbances such as changes in a surrounding environment of the agricultural crop (e.g., wind or rain blowing against the fruit of the agricultural crop). Therefore, by sensing the growth degree of the fruit of the agricultural crop based on the resonance frequency of the vibration of the agricultural crop, it is possible to sense the growth degree of the fruit of the agricultural crop more accurately than the method of directly measuring the mass of the fruit of the agricultural crop which is likely to be affected by the disturbances.

Further, when the agricultural crop is vibrated, the frequency spectrum obtained from the vibration information related to the vibration of the agricultural crop may contain a plurality of local maximum values caused by some factors other than the mass of the fruit of the agricultural crop (such as a mass of a wire for training the agricultural crop and the masses of the vibration device and the sensor each attached to the stem of the agricultural crop) in addition to the local maximum value (the resonance frequency) caused by the mass of the fruit of the agricultural crop. In the present invention, the one local maximum value among the plurality of local maximum values contained in the frequency spectrum obtained from the vibration information related to the vibration of the agricultural crop is identified as the resonance frequency of the vibration of the agricultural crop. Therefore, it is possible to perform only the measurement for the fruit of the agricultural crop which is a measurement target and exclude the local maximum values (the resonance frequencies) caused by the factors other than the mass of the fruit of the agricultural crop from the measurement target.

Furthermore, in a case where the agricultural crop has a plurality of fruits, the values of the resonance frequencies respectively caused by the masses of the plurality of fruits are different from each other depending on the growth degree of each fruit. In this case, by identifying local maximum values respectively corresponding to the plurality of fruits among the plurality of local maximum values contained in the frequency spectrum obtained from the vibration information related to the vibration of the agricultural crop as resonance frequencies of the vibration of the agricultural crop, it is possible to simultaneous Furthermore, in the case of directly measuring the mass of the fruit of the agricultural crop, it is required to bring a measuring instrument such as a scale into contact with the fruit of the agricultural crop. In this case, there is a risk that the fruit of the agricultural crop is damaged due to the contact with the measuring instrument. On the other hand, the vibration device and the sensor used in the present invention are attached to the stem of the agricultural crop and do not contact with the fruit of the agricultural crop. Therefore, it is possible to sense the growth degree of the fruit of the agricultural crop without making the measuring instrument contact with the fruit of the agricultural crop and thus there is no risk that the fruit of the agricultural crop is damaged and the commodity value of the fruit is lowered.

Furthermore, in the case of directly measuring the mass of the fruit of the agricultural crop, the agricultural operator needs to hold the fruit of the agricultural crop one by one with a hand each measurement time to measure the mass of the fruit. If the number of fruits is large, this work requires a great amount of labor and thus this work is a great burden on the agricultural operator. On the other hand, in the present invention, once the vibration device and the sensor are attached to the stem of the agricultural crop, it is not necessary to remove the vibration device and the sensor thereafter. The measurement for the growth degree of the agricultural crop can be automatically performed at a predetermined cycle or can be performed at an arbitrary timing according to an instruction from the computing device which controls the vibration device and the sensor. Therefore, once the vibration device and the sensor are attached to the agricultural crop stem, the labor of the agricultural operator for sensing the growth degree of the fruit of the agricultural crop becomes very small thereafter. Therefore, according to the present invention, it is possible to minimize the labor of the agricultural operator for sensing the growth degree of the fruit of the agricultural crop.

Furthermore, the information related to the growth degree of the fruit of the agricultural crop obtained by the present invention can be used in various applications described in the section on the background art and thus is useful for activities of the agricultural operator.

DETAILED DESCRIPTION

Hereinafter, a sensing system, a sensing method and a non-transitory computer readable medium according to the present invention will be described with reference to preferred embodiments shown in the accompanying drawings.

First Embodiment

Figure 1:
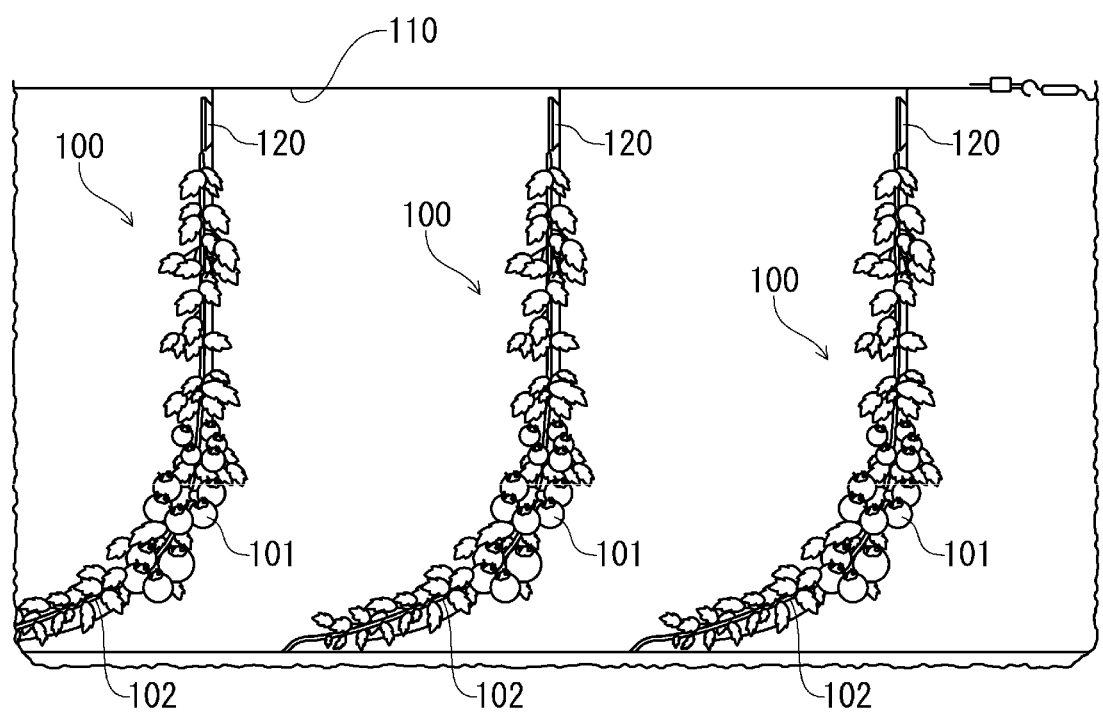
FIG. 1 is a conceptual diagram showing an agricultural crop cultivated by a training method for which a sensing system of the present invention is used.
Figure 2:
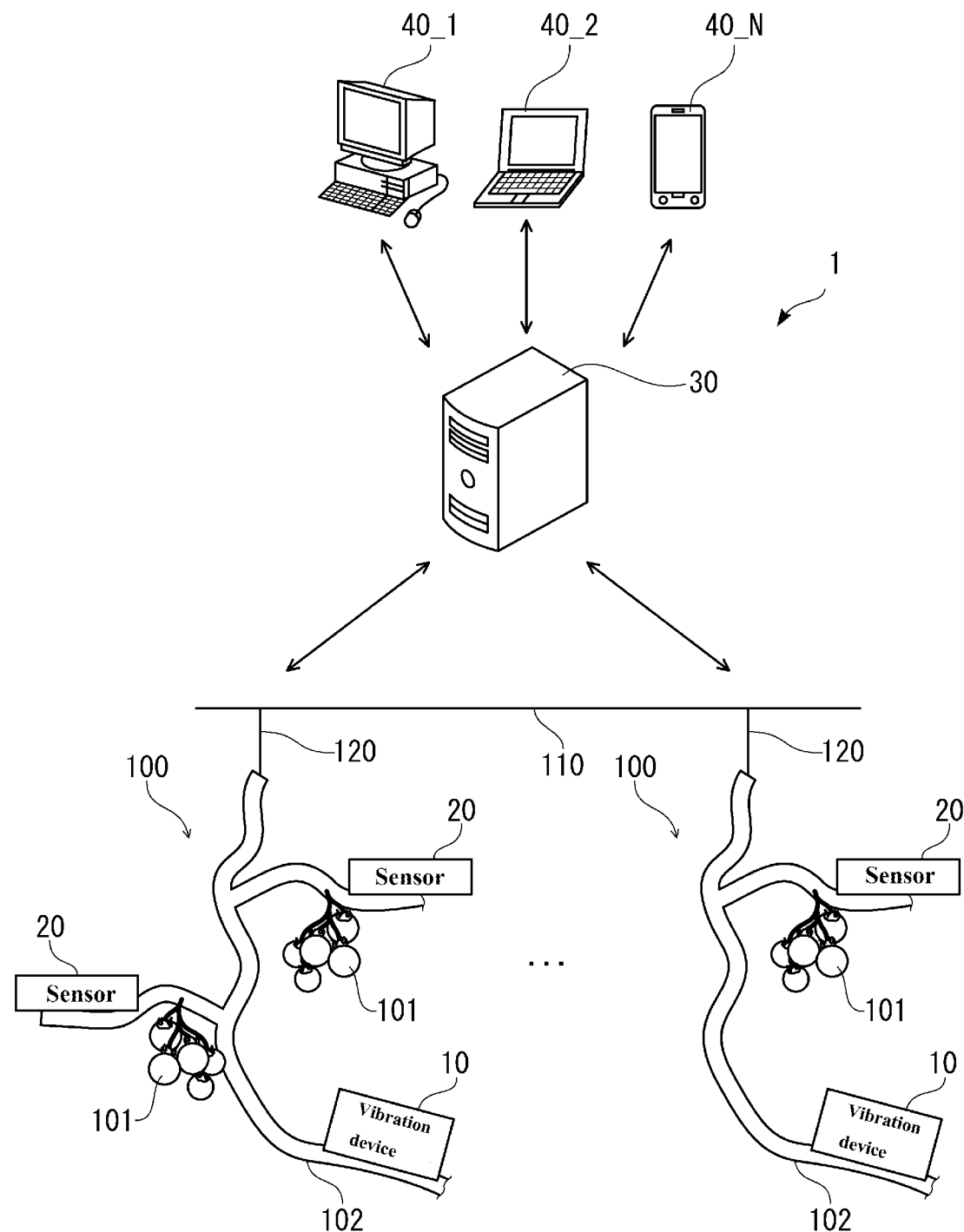
FIG. 2 is a conceptual diagram showing an embodiment of a sensing system according to a first embodiment of the present invention.
Figure 3:
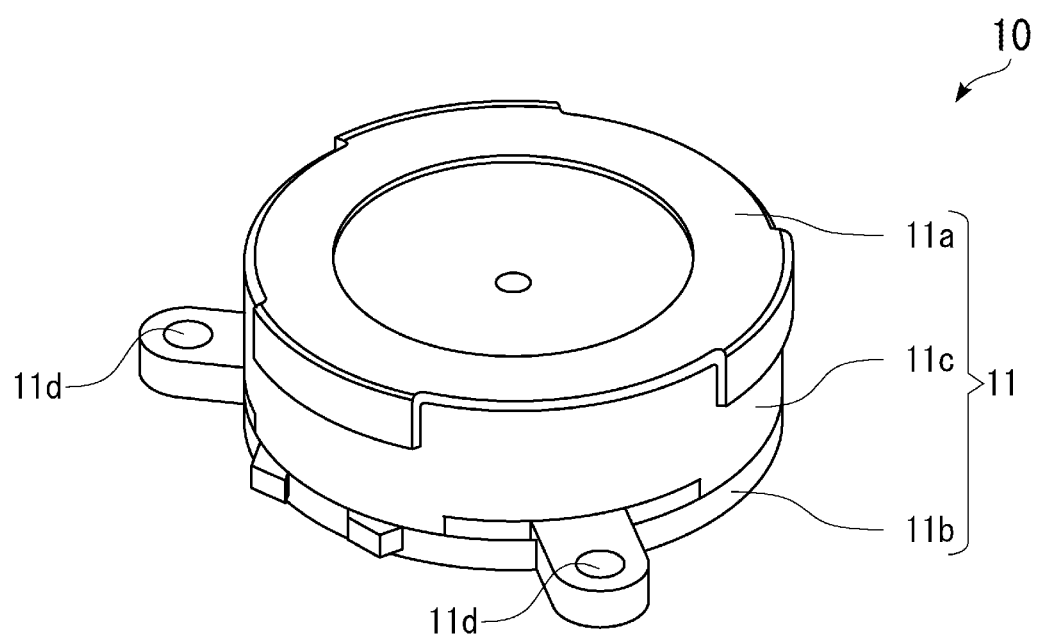
FIG. 3 is a perspective view of a vibration device shown in FIG. 2.
Figure 4:
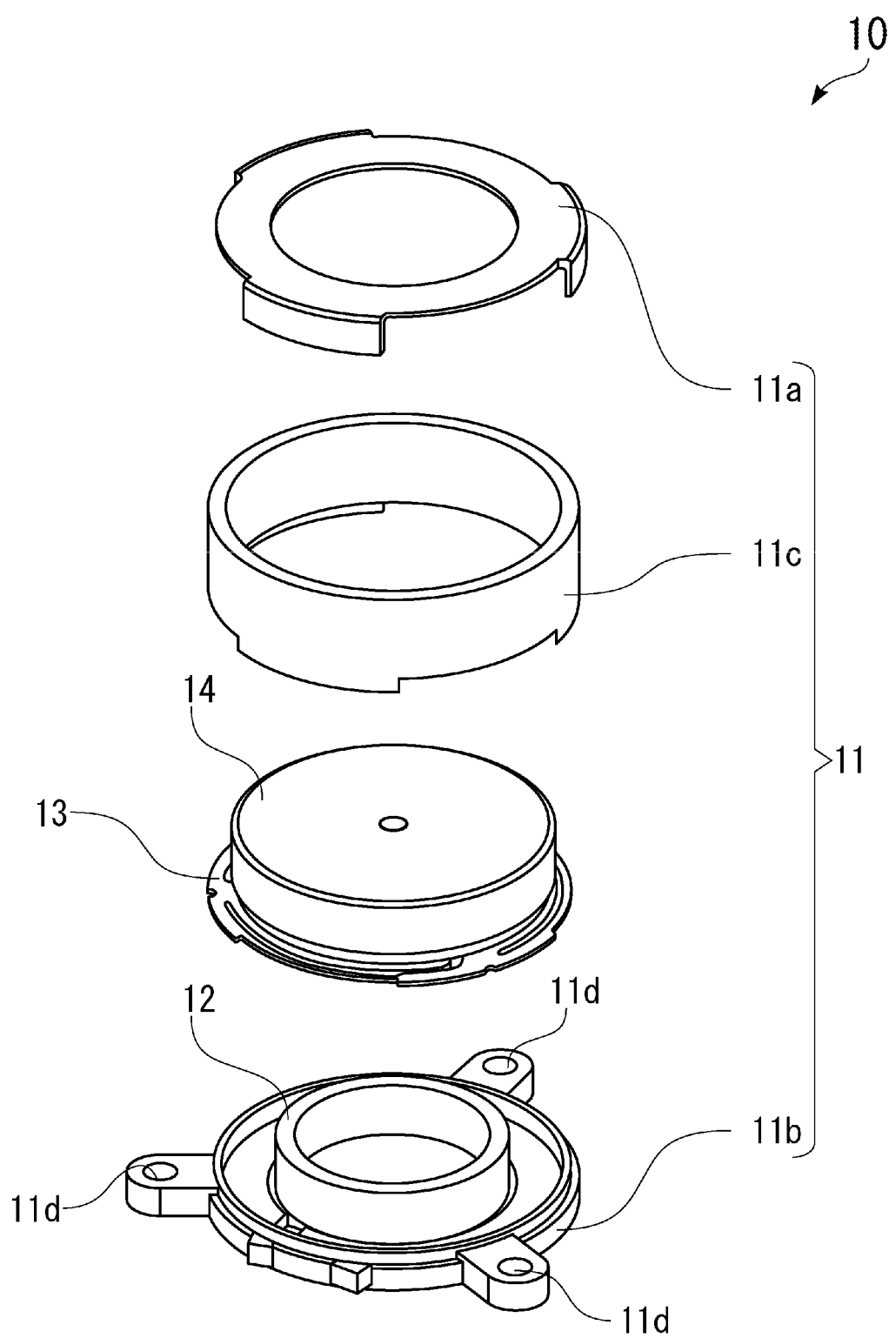
FIG. 4 is an exploded perspective view of the vibration device shown in FIG. 2.
Figure 5:
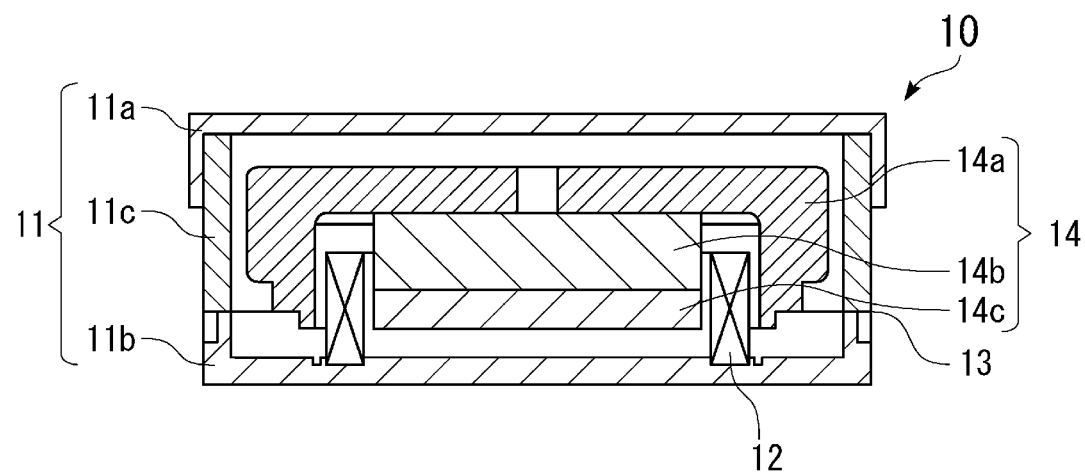
FIG. 5 is a cross-sectional view of the vibration device shown in FIG. 2.
Figure 6:
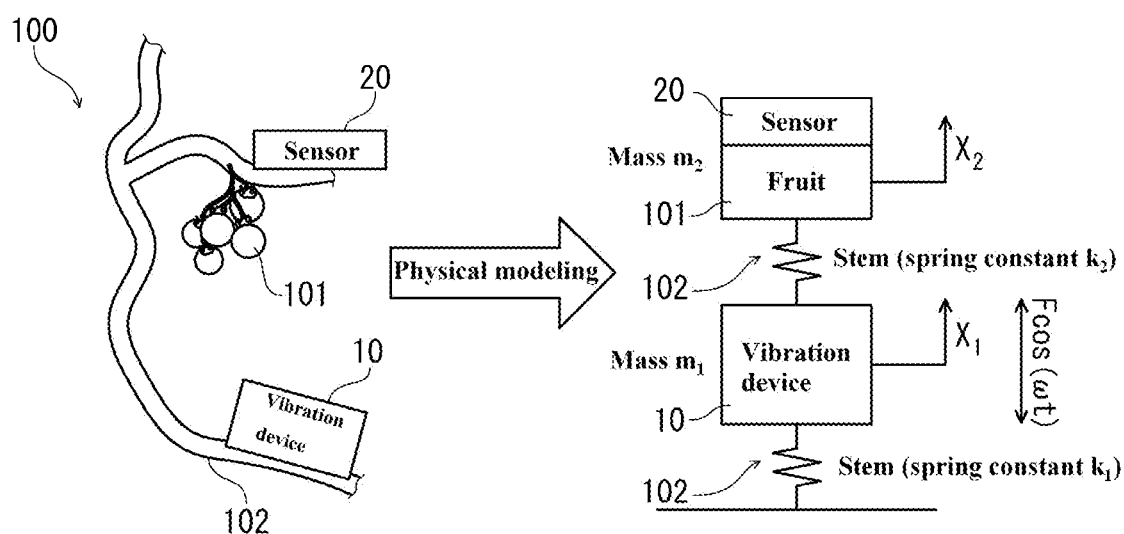
FIG. 6 is a diagram for explaining a physical model of a vibrating agricultural crop.
Figure 7:
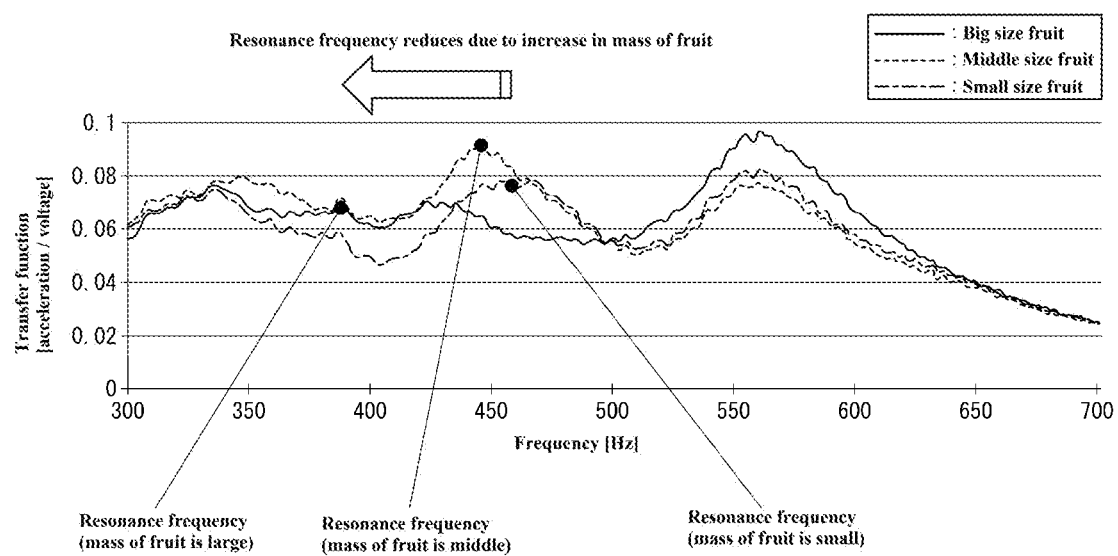
FIG. 7 is a diagram for explaining a change in a resonance frequency of vibration of the agricultural crop caused by increase in a mass of a fruit of the agricultural crop.
Figure 8:
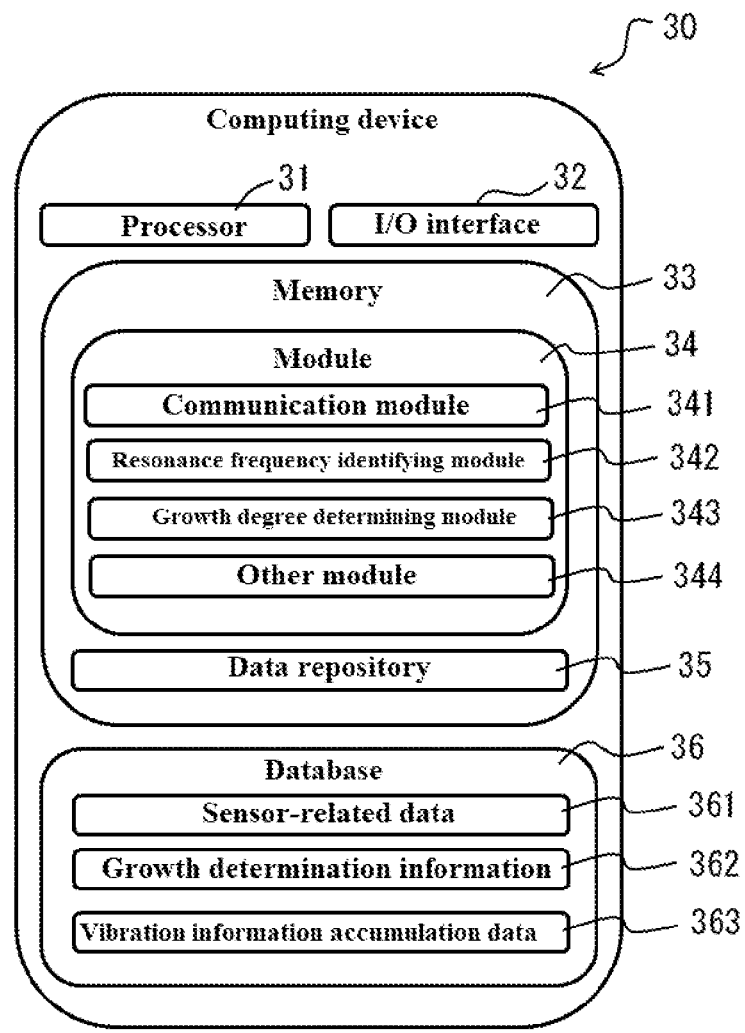
FIG. 8 is a block diagram of the computing device shown in FIG. 2.

FIG. 1 is a conceptual diagram showing an agricultural crop cultivated by a training method for which a sensing system of the present invention is used. FIG. 2 is a conceptual diagram showing an embodiment of a sensing system according to a first embodiment of the present invention. FIG. 3 is a perspective view of a vibration device shown in FIG. 2. FIG. 4 is an exploded perspective view of the vibration device shown in FIG. 2. FIG. 5 is a cross-sectional view of the vibration device shown in FIG. 2. FIG. 6 is a diagram for explaining a physical model of a vibrating agricultural crop. FIG. 7 is a diagram for explaining a change in a resonance frequency of vibration of the agricultural crop caused by increase in a mass of a fruit of the agricultural crop. FIG. 8 is a block diagram of the computing device shown in FIG. 2.

A sensing system 1 of the present invention is used for sensing a growth degree of a fruit 101 of an agricultural crop 100 cultivated by a training method as shown in FIG. 1. The agricultural crop 100 cultivated by the training method is a fruit vegetable such as tomato, eggplant, cucumber and pepper or a fruit-like vegetable such as strawberry, for example.

A wire 110 is horizontally bridged above the agricultural crop 100 cultivated by the training method. A tip end side portion of a stem 102 of the agricultural crop 100 is hanged from the wire 110 by a hanging tool 120 such as a wire or a vertical string. The fruit 101 fruits in the middle of the stem 102 hanged from the wire 110. The fruit 101 is cultivated in a state that the fruit 101 is suspended from the stem 102.

FIG. 2 schematically shows an embodiment of the sensing system 1 of the present invention. The sensing system 1 contains at least one vibration device 10 attached to the stem 102 of the agricultural crop 100 for applying vibration to the agricultural crop 100, at least one sensor 20 attached to the stem 102 of the agricultural crop 100 for sensing vibration of the agricultural crop 100 caused by the vibration applied to the agricultural crop 100 from the vibration device 10 to transmit vibration information related to the vibration of the agricultural crop 100 and a computing device 30 for identifying one local maximum value among a plurality of local maximum values in a frequency spectrum obtained from the vibration information received from the at least one sensor 20 as a resonance frequency of the vibration of the agricultural crop 100 to determine the growth degree of the fruit 101 of the agricultural crop 100 based on the identified resonance frequency.

The at least one vibration device 10 is attached to a root side portion of the stem 102 of the agricultural crop 100. On the other hand, the at least one sensor 20 is attached to the tip end side portion of the stem 102 of the agricultural crop 100. The fruit 101 of the agricultural crop 100 fruits at a point located between a point of the stem 102 of the agricultural crop 100 to which the sensor 20 is attached and a point of the stem 102 of the agricultural crop 100 to which the vibration device 10 is attached in a state that the fruit 101 is suspended from the point of the stem 102 of the agricultural crop 100.

A method of attaching the at least one vibration device 10 and the at least one sensor 20 to the stem 102 of the agricultural crop 100 is not particularly limited. For example, the at least one vibration device 10 and the at least one sensor 20 may be attached to the stem 102 of the agricultural crop 100 by any mechanical means such as clips, clamps or special jigs.

The at least one sensor 20 attached to the stem 102 of the agricultural crop 100 is used for sensing the growth degree of the fruit 101 fruiting at the point between the point of the stem 102 of the agricultural crop 100 to which the vibration device 10 is attached and the point of the stem 102 of the agricultural crop 100 to which the sensor 20 is attached.

The number of sensors 20 is not limited to one. The sensors 20 can be attached to the stem 102 by a number corresponding to the number of fruits 101 (or clusters of fruits 101) whose growth degrees should be measured. For example, in a case that a plurality of fruits 101 (or clusters of fruits 101) respectively fruit at a plurality of points of the stem 102, the sensors 20 can be attached to the stem 102 of the agricultural crop 100 at points respectively suitable (corresponding) for the plurality of fruits 101 (or clusters of fruits 101) whose growth degrees should be measured by a number corresponding to the plurality of fruits 101 (or clusters of fruits 101) whose growth degree should be measured.

Furthermore, the number of vibration devices 10 is also not limited to one. Any number of vibration devices 10 can be attached to the stem 102 at any points as long as a positional relationship that the vibration device 10 is attached to the stem 102 at points closer to the root side of the stem 102 than the fruit 101 which is a measurement target and the sensors 20 are attached to the stem 102 at points closer to the tip side of the stem 102 than the fruit 101 which is the measurement target is satisfied.

Further, the vibration device 10 and the sensor 20 are preferably arranged so as to be spaced apart from each other by at least 10 to 20 cm depending on a type of the agricultural crop 100 (more specifically, depending on a thickness and a hardness of the stem 102 of the agricultural crop 100 and a size of the fruit 101). If a separation distance between the vibration device 10 and the sensor 20 is smaller than the above-mentioned range, a main component of vibration sensed by the sensor 20 does not match with the vibration of the agricultural crop 100 but match with the vibration of the vibration device 10. Thus, the vibration of the agricultural crop 100 cannot be accurately sensed.

The separation distance between the vibration device 10 and the sensor 20 is preferably equal to or less than 2 m depending on the type of the agricultural crop 100 (more specifically, depending on the thickness and the hardness of the stem 102 of the agricultural crop 100 and the size of the fruit 101). When the separation distance between the vibration device 10 and the sensor 20 is larger than the above-mentioned value, the vibration of the agricultural crop 100 to be sensed by the sensor 20 becomes too small. Thus, the vibration of the agricultural crop 100 cannot be accurately sensed.

Further, a plurality of sets of the vibration device 10 and the sensor 20 satisfying the above-described positional relationship may be attached to a plurality of agricultural crops 100 as shown in FIG. 2. The computing device 30 can receive vibration information related to the vibration of each of the plurality of agricultural crops 100 from the sensors 20 respectively attached to the plurality of agricultural crops 100 and can analyze and determine the growth degrees of the fruits 101 of many agricultural crops 100 in an integrated manner.

The vibration device 10 includes a power supply (an internal power supply such as a battery or a wired external power supply) which is not shown in the drawings and a control unit (not shown) which receives a signal from the computing device 30 through wired communication or wireless communication and performs control of the vibration device 10. The vibration device 10 is configured to use electric power of the power supply (the internal power supply or the external power supply) to drive and apply the vibration to the agricultural crop 100 in response to the signal transmitted from the computing device 30 in a predetermined cycle (e.g., once a day, twice a day, once a month or the like) or at any timing. In this regard, the vibration device 10 may include a power generation unit that executes power generation using external energy such as vibration or solar light and may be driven using electric power generated by the power generation unit. In this case, the vibration device 10 may not have either the internal power source or the external power source.

As shown in FIGS. 3 to 5, the vibration device 10 is a VCM (Voice Coil Motor) type vibration device with a small size (e.g., height 30 mm×length 30 mm×width 30 mm). The vibration device 10 constitutes a single resonant system.

The vibration device 10 includes a case 11 configured to be attachable to the stem 102 of the agricultural crop 100 through the mechanical means such as clips, clamps and special jigs, a coil 12 which is fixedly provided on a bottom surface of the case 11 and to which the electric power is supplied from the power source (the internal power source or the external power source) or the power generation unit, a leaf spring 13 provided so as to be capable of vibrating with respect to the case 11 and a magnet assembly 14 mounted on the leaf spring 13 so as to be spaced apart from the coil 12.

The case 11 is a cylindrical member and has functions of fixing the vibration device 10 to the stem 102 of the agricultural crop 100 through the mechanical means such as clips, clamps and special jigs and containing each component of the vibration device 10 therein. The case 11 includes a cover 11a, a base 11b and a cylindrical portion 11c located between the cover 11a and the base 11b.

Three extending portions extending in a radial direction of the base 11b are formed on an outer peripheral surface of the base 11b. Through-holes 11d are respectively formed in tip end side portions of the three extending portions. Screws (not shown) are respectively passed through the through-holes 11d of the base 11b and screwed with screwed holes respectively formed in the mechanical means such as clips, clamps and special jigs. With this operation, the base 11b is fixed to the mechanical means such as clips, clamps and special jigs. The vibration device 10 is attached (fixed) to the stem 102 of the agricultural crop 100 by fixing the mechanical means such as clips or special jigs to the stem 102 of the agricultural crop 100. By attaching the vibration device 10 to the stem 102 of the agricultural crop 100, it becomes possible to transmit the vibration of the vibration device 10 to the agricultural crop 100 to vibrate the agricultural crop 100.

The coil 12 has a cylindrical shape and fixedly provided on the base 11b. Both ends (electrical signal supply ends) of the coil 12 are connected to the power supply or the power generation unit and thus current from the power supply or the power generation unit flows in the coil 12. Further, the coil 12 is located inside a central opening of the leaf spring 13 in a state that the vibration device 10 is assembled as shown in FIG. 5.

The leaf spring 13 has a ring shape with the central opening. An outer peripheral portion of the leaf spring 13 is held between the base 11b and the cylindrical portion 11c so that a central portion of the leaf spring 13 containing the central opening can be vibrated with respect to the case 11 in the vertical direction of FIG. 5. The magnet assembly 14 is mounted on the central portion of the leaf spring 13 and thus the magnet assembly 14 can be vibrated with respect to the coil 12.

As shown in FIG. 5, the magnet assembly 14 includes a magnet holding portion 14a having a cylindrical shape which opens toward the lower side of FIG. 5, a magnet 14b fixed to a central lower surface of the magnet holding portion 14a and a yoke 14c attached to a lower surface of the magnet 14b.

As shown in FIG. 5, the magnet 14b and the yoke 14c are arranged inside a central hollow portion of the coil 12 so as to be spaced apart from the coil 12 in the state that the vibration device 10 has been assembled. When the current is supplied from the power supply or the power generation unit to the coil 12, driving force for moving the magnet assembly 14 (the magnet 14b) in the vertical direction of FIG. 5 is generated. Since the magnet assembly 14 is mounted on the leaf spring 13 which is provided so that the magnet assembly 14 can be vibrated, the magnet assembly 14 is vibrated in the vertical direction.

Thus, when the current is supplied from the power source or the power generation unit to the coil 12 of the vibration device 10 and the current flows in the coil 12, the vibration device 10 vibrates. A motion equation representing an operating principle of the single resonant system such as the vibration device 10 can be expressed by the following equation

[Eq. 1]

$$m\frac{d^2 x(t)}{dt^2} = K_f i(t) - K_{sp} x(t) - D\frac{dx(t)}{dt} \quad (1)$$

Here, m is a mass [kg] of the magnet assembly 14 (vibrator), x(t) is a displacement amount [m] of the magnet assembly 14 (vibrator), $K_f$ is a thrust constant [N/A] of the single resonant system, i(t) is the current [A] flowing in the coil 12, $K_{sp}$ is a spring constant [N/m] of the leaf spring 13 and D is a damping coefficient [N/(m/s)] of the single resonant system.

Further, a circuit equation representing the operating principle of the single resonant system such as the vibration device 10 can be expressed by the following equation (2).

[Eq. 2]

$$e(t) = Ri(t) + L\frac{di(t)}{dt} + K_e\frac{dx(t)}{dt} \quad (2)$$

Here, e(t) is a voltage [V] applied to the coil 12, R is a resistance [Ω] of the coil 12, L is an inductance [H] of the coil 12 and $K_e$ is a counter-electromotive force constant [V/(m/s)] of the single resonant system.

Thus, the vibration device 10 can be driven by using the power of the power source or the generating unit to apply the vibration to the agricultural crop 100 in response to the signal transmitted from the computing device 30 at a predetermined cycle (e.g., once a day, twice a day, once a month, etc.) or any timing.

FIG. 6 shows a physical model of the agricultural crop 100 which is vibrated by the vibration applied from the vibration device 10. The vibration device 10 and the sensor 20 are attached to the stem 102 of the agricultural crop 100 so as to satisfy the positional relationship as described above. The agricultural crop 100 vibrated by the vibration applied from the vibration devices 10 can be considered as a double resonant system as shown on the right side of FIG. 6.

A motion equation for the vibration of this double resonant system can be expressed by the following equations (3) and (4) with a spring constant $k_1$ [N/m] of the stem 102 from the root of the stem 102 to the point to which the vibration device 10 is attached, a mass $m_1$ [g] of the vibration device 10, a spring constant $k_2$ [N/m] of the stem 102 from the point to which the vibration device 10 is attached to the point at which the fruit 101 fruits and a total mass $m_2$ [g] of the sensor 20 and the fruit 101.

[Eq. 3]

$$m_1\ddot{x}_1 = -k_1 x_1 + k_2(x_2 - x_1) \quad (3)$$

$$m_2\ddot{x}_2 = -k_2(x_2 - x_1) \quad (4)$$

Here, $x_1$ is a displacement amount [m] of the fruit 101 and $x_2$ is a displacement amount [m] of the vibration device 10.

When $x_1 = A\cos(\omega t)$ and $x_2 = B\cos(\omega t)$ are defined as elementary solutions for these motion equations (3) and (4), a characteristic equation can be obtained as the following equation (5).

[Eq. 4]

$$\omega = \sqrt{\frac{1}{2}\left\{\frac{k_1 + k_2}{m_1} + \frac{k_2}{m_2} \mp \sqrt{\left(\frac{k_1 + k_2}{m_1} + \frac{k_2}{m_2}\right)^2 - \frac{4k_1 k_2}{m_1 m_2}}\right\}} \quad (5)$$

$$f = \frac{\omega}{2\pi}$$

Here, ω is a natural angular frequency and f is a resonance frequency.

As is clear from the above characteristic equation (5), when the total mass $m_2$ of the fruit 101 and the sensor 20 increases, the resonance frequency f of the vibration of the agricultural crop 100 reduces. In the embodiment of the sensing system 1 of the present invention shown in FIG. 2, since the mass of the sensor 20 is constant, a change in the total mass $m_2$ can be considered as a change in the mass of the fruit 101 of the agricultural crop 100. Thus, when the growth of the fruit 101 of the agricultural crop 100 progresses and the mass of the fruit 101 increases, the resonance frequency f of the vibration of the agricultural crop 100 shifts to the low frequency side.

Next, a relationship between the resonance frequency f of the vibration of the agricultural crop 100 and a transfer function (acceleration/voltage) of each frequency of the vibration of the agricultural crop 100 caused by the voltage applied to the vibration device 10 will be described below.

Motion equations in the case that the vibration device 10 applies the vibration to the agricultural crop 100 with sinusoidal excitation force (=F cos(ωt)) can be represented by the following equations (6) and (7).

[Eq. 5]

$$m_1\ddot{x}_1 + (k_1 + k_2)x_1 - k_2 x_2 = F\cos\omega t \quad (6)$$

$$m_2\ddot{x}_2 - k_2 x_1 + k_2 x_2 = 0 \quad (7)$$

When $x_1 = A\cos(\omega t)$ and $x_2 = B\cos(\omega t)$ are defined as elementary solutions for these motion equations (6) and (7) and a characteristic equation is obtained, constants A and B of the elementary solutions can be represented by the following equations (8) and (9.)

[Eq. 6]

$$A = \frac{(-m_2\omega^2 + k_2)F}{m_1 m_2[\omega^4 - \{(k_1 + k_2)/m_1 + k_2/m_2\}\omega^2 + k_1 k_2/(m_1 m_2)]} \quad (8)$$

$$B = \frac{k_2 F}{m_1 m_2[\omega^4 - \{(k_1 + k_2)/m_1 + k_2/m_2\}\omega^2 + k_1 k_2/(m_1 m_2)]} \quad (9)$$

Here, we define as follows.

$$\Omega_1 = \sqrt{k_1/m_1}$$

$$\Omega_2 = \sqrt{k_2/m_2}$$

$$X_{st} = F/k_1 \quad [\text{Eq. 7}]$$

Then, a transfer function of a vibration system of the mass $m_1$ and a transfer function of a vibration system of the mass $m_2$ constituting the double resonance system can be respectively represented by $A/X_{st}$ and $B/X_{st}$ as shown in the following equations (10) and (11).

[Eq. 8]

$$\frac{A}{X_{st}} = \frac{1 - (\omega/\Omega_2)^2}{\{(\omega/\Omega_1)^2 - (\omega_1/\Omega_1)^2\}\{(\omega/\Omega_2)^2 - (\omega/\Omega_2)^2\}} \quad (10)$$

$$\frac{B}{X_{st}} = \frac{1}{\{(\omega/\Omega_1)^2 - (\omega_1/\Omega_1)^2\}\{(\omega/\Omega_2)^2 - (\omega/\Omega_2)^2\}} \quad (11)$$

Here, $\omega_1$ and $\omega_2$ are natural angular frequencies w in the above equation (5).

As is clear from the above equation (11), the transfer function $B/X_{st}$ of the vibration system of the mass $m_2$ becomes large when the angular frequency ω (frequency) is in the vicinities of the natural angular frequencies $ω_1$ and $ω_2$ (the resonant frequencies f) obtained from the above equation (5). Therefore, it is possible to calculate the resonance frequency f (the natural angular frequency ω) of the vibration of the agricultural crop 100 by obtaining a local maximum value of the transfer function for each frequency of the vibration of the agricultural crop 100 (more specifically, the vibration of the vibration system for the mass $m_2$ of the double resonant system).

As is clear from the above equations (5) and (11), each of the resonance frequency f and the transfer function of the vibration of the agricultural crop 100 does not have any terms corresponding to disturbances such as changes in a surrounding environment of the agricultural crop 100 (for example, blowing of wind and rain against the fruit 101 of the agricultural crop 100). This means that the resonance frequency f and the transfer function of the vibration of the agricultural crop 100 are not affected by the disturbances against the fruit 101 of the agricultural crop 100.

Therefore, by sensing the growth degree of the fruit 101 of the agricultural crop 100 based on the resonance frequency f of the agricultural crop 100, it is possible to sense the growth degree of the fruit 101 of the agricultural crop 100 more accurately than the case of directly measuring the mass of the fruit 101 of the agricultural crop 100 which is likely to be affected the disturbances.

As described above, since the resonance frequency f of the vibration of the agricultural crop 100 changes according to the mass (the growth degree) of the fruit 101 of the agricultural crop 100, the mass (the growth degree) of the fruit 101 of the agricultural crop 100 can be sensed by calculating the resonance frequency f of the vibration of the agricultural crop 100 from the local maximum value of the transfer function of each frequency of the vibration of the agricultural crop 100.

FIG. 7 shows an example in which the local maximum value (i.e., the resonance frequency f) of the transfer function of each frequency of the vibration of the agricultural crop 100 changes according to the growth (the increase in mass) of the fruit 101 of agricultural crop 100. The graph shown in FIG. 7 is a frequency spectrum obtained from the vibration of the agricultural crop 100.

As shown in FIG. 7, the frequency spectrum obtained from the vibration of the agricultural crop 100 contains a plurality of local maximum values. For example, in the frequency spectrum for the case of the growth degree of the fruit 101 progresses (the fruits 101 is big) which is illustrated by a solid line in FIG. 7, the local maximum values respectively exist in the vicinities of 340 Hz, 390 Hz, 430 Hz and 570 Hz. The local maximum value caused by the fruit 101 of the agricultural crop 100 in the frequency spectrum can be predicted to some extent from prior information that can be obtained in advance. The prior information contains a predicted mass of the fruit 101 of the agricultural crop 100, a type of the agricultural crop 100, a period from planting the agricultural crop 100 and the like. Further, it can be understood from FIG. 7 that the local maximum value caused by the fruit 101 of the agricultural crop 100 shifts to the low frequency side as the growth of the fruit 101 of the agricultural crop 100 progresses (as the mass of the fruit 101 increases). On the other hand, the local maximum values caused by some factors other than the mass of the fruit 101 of the agricultural crop 100 (such as the mass of the wire 110 for training the agricultural crop 100 and the masses of the vibration device 10 and the sensor 20 each attached to the stem 102 of the agricultural crop 100) do not substantially shift.

In the present invention, one local maximum value among the plurality of local maximum values contained in the frequency spectrum is identified as the resonance frequency f of the agricultural crop 100 based on prediction from the prior information that can be obtained in advance or the shift amount of the local maximum value described above. Therefore, it is possible to perform only the measurement for the fruit 101 of the agricultural crop 100 which should be measured and exclude the local maximum values (the resonance frequencies) caused by the factors other than the mass of the fruit 101 of the agricultural crop 100 from the measurement target.

As described above, since the local maximum value caused by the fruit 101 of the agricultural crop 100 shifts to the low frequency side as the growth of the fruit 101 of the agricultural crop 100 progresses (as the mass of the fruit 101 increases), the growth of the fruit 101 of the agricultural crop 100 can be sensed by identifying the local maximum value (i.e., the resonance frequency f) caused by the fruit 101 of the agricultural crop 100.

As described above, by applying the vibration to the agricultural crop 100 with the vibration device 10 attached to the stem 102 of the agricultural crop 100 and identifying one local maximum value among the plurality of local maximum values in the frequency spectrum obtained from the vibration information related to the vibration of the agricultural crop 100 caused by the applied vibration as the resonance frequency f of the vibration of the agricultural crop 100, the increase in the mass of the fruit 101 of the agricultural crop 100, i.e., the growth degree of the fruit 101 of the agricultural crop 100 can be sensed.

Further, in the case that there are a plurality of fruits 101 between the point of the stem 102 of the agricultural crop 100 to which the vibration device 10 is attached and the point of the stem 102 of the agricultural crop 100 to which the sensor 20 is attached, the frequency spectrum obtained from the vibration of the agricultural crop 100 contains a plurality of local maximum values respectively corresponding to the masses of the plurality of fruits 101. In this case, by identifying the plurality of local maximum values respectively corresponding to the masses of the plurality of fruits 101 as the resonance frequencies f of the vibration of the agricultural crop 100, it is possible to simultaneously sense the growth degrees of the plurality of fruits 101.

Referring back to FIG. 2, the sensor 20 is attached to the tip end portion of the stem 102 of the agricultural crop 100. The sensor 20 is configured to sense the vibration of the agricultural crop 100 caused by the vibration applied to the agricultural crop 100 from the vibration device 10 and transmit the vibration information related to the vibration of the agricultural crop 100 to the computing device 30 through the wired communication or the wireless communication.

The sensor 20 includes a power source (for example, an internal power source such as a battery or a wired external power source) or a power generation unit which is not shown in the drawings as is the case with the vibration device 10 and a control unit (not shown) which communicates with the computing device 30 through the wired communication or the wireless communication to perform control of the sensor 20. The sensor 20 is driven at the same timing as the vibration device 10 by using electric power of the power source (the internal power source or the external power source) or the power generation unit in response to the signal transmitted from the computing device 30 at the predetermined cycle (e.g., once every day, twice every day, once every month, etc.) or any timing. The sensor 20 senses the vibration of the agricultural crop 100 caused by the vibration applied from the vibration device 10 to transmit the vibration information related to the vibration of the agricultural crop 100 to the computing device 30 through the wired communication or the wireless communication.

The vibration information transmitted from the sensor 20 to the computing device 30 contains data (such as raw data of vibration) required for allowing the computing device 30 to calculate the resonance frequency f of the vibration of the agricultural crop 100. Further, the sensor 20 transmits sensor identification information such as a sensor ID to the computing device 30 for allowing the computing device 30 to identify the sensor 20 at the same time of transmitting the vibration information. Furthermore, the sensor 20 may transmit any other information which is useful for determining the growth degree of the fruit 101 of the agricultural crop 100 when the computing device 30 determines it together with the vibration information and the sensor identification information to the computing device 30.

The data required for allowing the computing device 30 to calculate the resonance frequency f of the vibration of the agricultural crop 100 is data related to an acceleration of the vibration (motion) of the agricultural crop 100, for example. The computing device 30 can perform a process such as the Fourier transform on the obtained data to obtain the frequency spectrum representing the transfer function (or energy) of each frequency of the vibration of the agricultural crop 100. Thus, the computing device 30 can identify one local maximum value among the plurality of local maximum values of the transfer function (or energy) of each frequency of the vibration of the agricultural crop 100 contained in the obtained frequency spectrum as the resonance frequency f of vibration of the agricultural crop 100.

The sensor 20 is not particularly limited as long as it can sense the vibration of the agricultural crop 100 to transmit the vibration information related to the vibration of the agricultural crop 100 and the sensor identification information to the computing device 30. For example, an acceleration sensor, a strain sensor or the like can be used as the sensor 20.

The computing device 30 is configured to transmit the drive signals to the vibration device 10 and the sensor 20 at the predetermined cycle or any timing for driving the vibration device 10 and the sensor 20, receive the vibration information related to the vibration of the agricultural crop 100 from the sensor 20 and identify one maximum value among the plurality of local maximum values in the frequency spectrum obtained from the received vibration information as the resonance frequency f of the vibration of the agricultural crop 100 to determine the growth degree of the fruit 101 of the agricultural crop 100 based on the identified resonance frequency f.

Further, the computing device 30 is configured to transmit the determination for the growing degree of the fruit 101 of the agricultural crop 100 to any number of user devices 40_1, 40_2, . . . , 40_N of users using the sensing system 1 (hereafter, referred to as the user device 40 collectively) through the wired communication or the wireless communication. For example, the user device 40 may be any information terminal device such as a desktop computer, a laptop computer, a notebook computer, a workstation, a tablet computer, a mobile phone, a smartphone, a PDA or the like. The user device 40 receives the determination for the growth degree of the fruit 101 of the agricultural crop 100 from the computing device 30 through the wired communication or the wireless communication.

The user using the sensing system 1 uses his/her user device 40 to check the determination for the growth degree of the fruit 101 of the agricultural crop 100 transmitted from the computing device 30. Thus, the user can know useful information for agriculture such as whether or not the fruit 101 of the agricultural crop 100 has grown to a size to be harvested, whether or not there is an abnormality in the growth of the fruit 101 of the agricultural crop 100 and when the fruit 101 of the agricultural crop 100 can be harvested.

The computing device 30 may be implemented as a single device or in any computing device such as a desktop computer, a laptop computer, a notebook computer, a workstation, a tablet computer, a mobile phone, a smartphone, a PDA, a wearable terminal or the like.

As shown in FIG. 8, the computing device 30 contains at least one processor 31 which performs control of the computing device 30, an I/O (input and output) interface 32, at least one memory 33 which is communicatively coupled to the processor 31 and stores data, programs, modules and the like required for performing the control of the computing device 30 and a database 36 communicatively coupled to the processor 31. The components of the computing device 30 are communicatively interconnected to each other through various buses such as a system bus.

The processor 31 is an arithmetic unit such as one or more microprocessors, microcomputers, microcontrollers, digital signal processors (DSPs), central processing units (CPUs), memory control units (MCUs), image processing units (GPUs), state-machines, logical circuits, application-specific integrated circuits (ASIC) or combinations thereof which can perform arithmetic processes such as signal manipulation based on computer readable instructions. In particular, the processor 31 is configured to fetch computer readable instructions (e.g., data, programs and modules) stored in the memory 33 to perform signal manipulation and signal control.

The I/O interface 32 is any kind of software interfaces such as a web interface and a graphical user interface (GUI) or any kind of hardware interfaces. The I/O interface 32 allows the computing device 30 to interact with the vibration device 10, the sensor 20, the user device 40 and any other external devices and allows the user to access the computing device 30. Further, the I/O interface 32 may enable the computing device 30 to communicate with any external device such as a web server or data server externally provided through any network such as the Internet.

If the computing device 30 is connected with the vibration device 10, the sensor 20, the user device 40 and any external device through a wired connection, the computing device 30 performs the wired communication with the vibration device 10, the sensor 20, the user device 40 and the external device. If the computing device 30 is not connected to the vibration device 10, the sensor 20 the user device 40 and the external device through the wired communication, the computing device 30 wirelessly communicates with the vibration device 10, the sensor 20, the user device 40 and the external device with a radio communication technique such as NFC (Near Field Radio Communication), Wi-Fi, Bluetooth (registered trademark) or the like.

The memory 33 is a removable or non-removable computer readable medium containing a volatile storage medium (e.g., RAM, SRAM, DRAM), a non-volatile storage medium (e.g., ROM, EPROM, EEPROM, flash memory, hard disk, optical disc, CD-ROM, digital versatile disc (DVD), magnetic cassette, magnetic tape, magnetic disk) and a combination thereof.

The memory 33 stores a plurality of modules 34 which can be executed by the processor 31 and further contains a data repository 35 for storing data received, processed or generated by one or more of the plurality of modules 34 and other data required for performing processes of the computing device 30.

The modules 34 are computer readable instructions which can be executed by the processor 31 such as routines, applications, programs, algorithms, libraries, objects, components, structures and combinations thereof.

The database 36 is any non-volatile storage medium (e.g., a hard disk, a server and a flash memory) which stores the sensor identification information of each sensor 20, sensor-related data 361 for each sensor 20 (such as information on the agricultural crop 100 to which each sensor 20 is attached, information on the position of the stem 102 to which each sensor 20 is attached and an attachment date and time of each sensor 20 and the like), growth determination information 362 which is one or more parameters required for determining the growth degree of the fruit 101 of the agricultural crop 100 and vibration information accumulation data 363 which is constituted by accumulating the vibration information transmitted from each sensor 20 to the computing device 30.

Hereinafter, the modules 34 used by the processor 31 for providing the functions of the computing device 30 will be described below.

The modules 34 contain a communication module 341 for performing communication between the computing device 30 and the vibration device 10, the sensor 20, the user device 40 or any external device, a resonance frequency identifying module 342 for identifying one local maximum value among the plurality of local maximum values in the frequency spectrum obtained from the vibration information related to the vibration of the agricultural crop 100 received from the sensor 20 as the resonance frequency f of the vibration of the agricultural crop 100, a growth degree determining module 343 for determining the growth degree of the fruit 101 of the agricultural crop 100 based on the resonance frequency f of the vibration of the agricultural crop 100 identified by using the resonance frequency identifying module 342 and any number of other modules 344 for compensating the functions provided by the computing device 30.

The processor 31 can provide the desired functions by executing the various modules 34 stored in the memory 33. For example, the processor 31 can use the communication module 341 to perform the communication with the vibration device 10, the sensor 20, the user device 40 and the external device.

The communication module 341 is used for performing the communication between the computing device 30 and the vibration device 10, the sensor 20, the user device 40 or the external device. The computing device 30 uses the communication module 341 to transmit the drive signals to the vibration device 10 and the sensor 20 at the predetermined cycle or any timing. At this case, the computing device 30 may refer to the sensor-related data 361 stored in the database 36 to simultaneously drive all of the sensors 20 and the vibration devices 10 corresponding to all of the sensors 20 or drive only one or more sensors 20 and the vibration devices 10 corresponding to the sensors 20 to be driven.

When the vibration device 10 receives the drive signal from the computing device 30, the vibration device 10 drives by using electric power of its own power source or the generating unit to apply the vibration to the agricultural crop 100. At this time, a frequency of the vibration of the vibration device 10 is appropriately set depending on the type of the agricultural crop 100 (more specifically, depending on the thickness and the hardness of the stem 102 of the agricultural crop 100 and the size of the fruit 101). For example, if the agricultural crop 100 is tomato, the vibration device 10 vibrates with a frequency in the range of about 400 to 800 Hz.

When the agricultural crop 100 is vibrated by the vibration applied from the vibration device 10, the sensor 20 senses the vibration of the agricultural crop 100 and transmits the vibration information related to the vibration of the agricultural crop 100 to the computing device 30. The computing device 30 uses the communication module 341 to receive the vibration information related to the vibration of the agricultural crop 100 from the sensor 20. The vibration information received by the vibration device 10 is associated with the sensor identification information (e.g., the sensor ID) for identifying the sensor 20 which transmits the vibration information and any data which is useful for analyzing the growth of the fruit 101 of the agricultural crop 100. After that, the vibration information is stored as the vibration information accumulation data 363.

The vibration information accumulation data 363 is so-called big data related to the growth of the fruit 101 of the agricultural crop 100. The vibration information accumulation data 363 can be utilized in an application which is useful for an agricultural operator and can be utilized for extracting information which is useful for the agricultural operator.

The resonance frequency identifying module 342 is used for identifying one local maximum value among the plurality of local maximum values in the frequency spectrum obtained from the vibration information related to the vibration of the agricultural crop 100 received from the sensor 20 as the resonance frequency f of the vibration of the agricultural crop 100. A method of identifying the resonance frequency f of the vibration of the agricultural crop 100 from the vibration information is not particularly limited. For example, if the vibration information contains acceleration information of the vibration of the agricultural crop 100, the resonance frequency identifying module 342 performs the Fourier transform on the acceleration information of the vibration of the agricultural crop 100 to obtain the frequency spectrum representing the transfer function (or power) of each frequency of the vibration of the agricultural crop 100. After that, the resonance frequency identifying module 342 can identify the one local maximum value among the plurality of local maximum values contained in the frequency spectrum as the resonance frequency f of the vibration of the agricultural crop 100 based on a predicted mass of the fruit 101 of the agricultural crop 100 derived from the prior information which can be obtained in advance (such as the type of the agricultural crop 100 and the period after the agricultural crop 100 is planted) and/or a shift amount of the local maximum value.

The growth degree determining module 343 is used for determining the growth degree of the fruit 101 of the agricultural crop 100 based on the resonance frequency f of the vibration of the agricultural crop 100 identified by using the resonance frequency identifying module 342. As described above, when the fruit 101 of the agricultural crop 100 has grown and the mass of the fruit 101 increases, the resonance frequency f of the vibration of the agricultural crop 100 shifts to the low frequency side. Thus, the growth degree determining module 343 determines that the fruit 101 of the agricultural crop 100 has grown to the size to be harvested when the resonance frequency f of the vibration of the agricultural crop 100 is equal to or less than a predetermined threshold value. In this regard, the predetermined threshold value is defined in advance depending on the type of the agricultural crop 100 (more specifically, depending on the thickness and the hardness of the stem 102 of the agricultural crop 100 and the size of the fruit 101) and stored in advance in the database 36 as one information constituting the growth determination information 362.

Further, the growth degree determining module 343 compares the resonance frequency f of the vibration of the agricultural crop 100 identified from the vibration information obtained in the previous measurement with the resonance frequency f of the vibration of the agricultural crop 100 identified from the vibration information obtained in the current measurement to determine whether or not an abnormality has occurred in the growth of the fruit 101 of the agricultural crop 100. Specifically, the growth degree determining module 343 compares the resonance frequency f of the vibration of the agricultural crop 100 identified from the vibration information obtained in the previous measurement with the resonance frequency f of the vibration of the agricultural crop 100 identified from the vibration information obtained in the current measurement to determine whether or not the resonance frequency f of the vibration of the agricultural crop 100 shifts to the low frequency side by a predetermined value or more and detects the abnormality in the growth of the fruit 101 of the agricultural crop 100 according to the result of this determination.

When the resonance frequency f of the vibration of the agricultural crop 100 does not shift to the low frequency side by the predetermined value or more, that is, a change amount Δf of the resonance frequency f of the vibration of the agricultural crop 100 is equal to or less than the predetermined value or the resonance frequency f of the vibration of the agricultural crop 100 shifts to the high frequency side, it is determined that a problem has occurred in the growth of the fruit 101 of the agricultural crop 100. When the change amount Δf of the resonance frequency f of the vibration of the agricultural crop 100 is equal to or less than the predetermined value, it is determined that the growth of the fruit 101 of the agricultural crop 100 does not progress fine. Further, when the resonance frequency f of the vibration of the agricultural crop 100 shifts to the high frequency side, it is determined that the mass of the fruit 101 of the agricultural crop 100 decreases due to one or more reasons that the fruit 101 falls from the stem 102, the fruit 101 is cracked or the like. In this regard, the predetermined value is defined in advance depending on the type of the agricultural crop 100 (more specifically, the thickness and the hardness of the stem 102 of the agricultural crop 100 and the size of the fruit 101) and stored in advance in the database 36 as one information constituting the growth determination information 362.

Further, when the resonance frequency f of the vibration of the agricultural crop 100 shifts to the low frequency side by the predetermined value or more but the resonance frequency f of the vibration of the agricultural crop 100 is larger than the predetermined threshold value, the growth degree determining module 343 determines that no problem has occurred in the growth of the fruit 101 but the fruit 101 has not grown to the size to be harvested. In this case of determining that no problem has occurred in the growth of the fruit 101 but the fruit 101 has not grown to the size to be harvested, the growth degree determining module 343 determines (predicts) a harvesting time for the fruit 101 based on a difference between the calculated resonance frequency f of the vibration of the agricultural crop 100 and the predetermined threshold value and/or the change amount Δf of the resonance frequency f of the vibration of the agricultural crop 100. A table or a mathematical equation for determining the harvest time for the fruit 101 from the difference between the calculated resonance frequency f of the vibration of agricultural crop 100 and the predetermined threshold value and/or the change amount Δf of the resonance frequency f of the vibration of agricultural crop 100 is predefined in advance and stored as one information constituting the growth determination information 362 in the database 36. The growth degree determining module 343 determines the harvest time for the fruit 101 by referring to this table or this mathematical equation.

The determination by the growth degree determining module 343 described above is transmitted to the user device 40 with the communication module 341. The user of the sensing system 1 can obtain information related to the growth of the fruit 101 of the agricultural crop 100 by referring to the determination transmitted to the user device 40 and can utilize this information in various applications as described in the section of the background art.

As described above, the sensing system 1 of the present invention uses the vibration device 10 to apply the vibration to the agricultural crop 100, uses the sensor 20 to sense the vibration of the agricultural crop 100 caused by the applied vibration, identifies one local maximum value among the plurality of local maximum values in the frequency spectrum obtained from the vibration information related to the vibration of the agricultural crop 100 as the resonance frequency f of the vibration of the agricultural crop 100 and senses the growth degree of the fruit 101 of the agricultural crop 100 based on the identified resonance frequency.

As described above, the resonance frequency f (and the transfer function) of the vibration of the agricultural crop 100 does not depend on the disturbances such as changes in the surrounding environment of the agricultural crop 100 (e.g., blowing wind or rain against the fruit of the agricultural crop). Therefore, by sensing the growth degree of the fruit 101 of the agricultural crop 100 based on the resonance frequency f of the vibration of the agricultural crop 100, it is possible to sense the growth degree of the fruit 101 of the agricultural crop 100 more accurately than the case of directly measuring the mass of the fruit 101 of the agricultural crop 100 which is likely to be affected by the disturbances.

Further, when the agricultural crop 100 is vibrated, the frequency spectrum obtained from the vibration information related to the vibration of the agricultural crop 100 may include a plurality of local maximum values caused by some factors (such as the mass of the wire 110 for training the agricultural crop 100 and the masses of the vibration device 10 and the sensor 20 attached to the stem 102 of the agricultural crop 100) other than the mass of the fruit 101 of the agricultural crop 100 in addition to the local maximum value (the resonance frequency f) caused by the mass of the fruit 101 of the agricultural crop 100. In the present invention, one local maximum value among the plurality of local maximum values contained in the frequency spectrum obtained from the vibration information related to the vibration of the agricultural crop 100 is identified as the resonance frequency of the vibration of the agricultural crop 100. Therefore, it is possible to perform only the measurement for the fruit 101 of the agricultural crop 100 which should be measured and exclude the local maximum values (the resonance frequencies) caused by the factors other than the mass of the fruit 101 of the agricultural crop 100 from the measurement target.

Further, in the case that there are a plurality of fruits 101 between the point of the stem 102 of the agricultural crop 100 to which the vibration device 10 is attached and the point of the stem 102 of the agricultural crop 100 to which the sensor 20 is attached, the frequency spectrum obtained from the vibration of the agricultural crop 100 contains a plurality of local maximum values respectively corresponding to the masses of the plurality of fruits 101. In this case, by identifying the plurality of local maximum values respectively corresponding to the masses of the plurality of fruits 101 as the resonance frequencies f of the vibration of the agricultural crop 100, it is possible to simultaneously sense the growth degrees of the plurality of fruits 101.

Furthermore, in the case of directly measuring the mass of the fruit 101 of the agricultural crop 100, it is required to bring the fruit 101 of the agricultural crop 100 into contact with the measuring instrument such as a scale. However, in this case, there is a risk that the fruit 101 of the agricultural crop 100 is damaged by the contact with the measuring instrument and thus the commodity value of the fruit 101 is lowered. On the other hand, the vibration device 10 and the sensor 20 used in the sensing system 1 of the present invention are attached to the stem 102 of the agricultural crop 100 and do not contact with the fruit 101 of the agricultural crop 100. Therefore, it is possible to sense the growth degree of the fruit 101 of the agricultural crop 100 without making the measuring instrument contact with the fruit 101 of the agricultural crop 100. Thus, there is no risk that the fruit 101 of the agricultural crop 100 is damaged and the commodity value of the fruit 101 is lowered.

Further, in the case of directly measuring the mass of the fruit 101 of the agricultural crop 100, the agricultural operator needs to hold the fruit 101 of the agricultural crop 100 one by one with a hand and measure the mass of the fruit 101 each measurement time. If the number of the fruit 101 is large, such an operation requires a great amount of labor and thus this operation is a great burden for the agricultural operator. On the other hand, in the sensing system 1 of the present invention, once the vibration device 10 and the sensor 20 are attached to the stem 102 of the agricultural crop 100, it is not necessary to remove the vibration device 10 and the sensor 20 thereafter. The measurement of the growth degree of the fruit 101 of the agricultural crop 100 can be automatically performed at the predetermined cycle or can be performed at any timing according to a command from the computing device 30 which controls the vibration device 10 and the sensor 20. Therefore, once the vibration device 10 and the sensor 20 are attached to the stem 102 of the agricultural crop 100, the labor of the agricultural operator for sensing the growth degree of the fruit 101 of the agricultural crop 100 becomes very small. Therefore, according to the sensing system 1 of the present invention, it is possible to minimize the labor of the agricultural operator for sensing the growth degree of the fruit 101 of the agricultural crop 100.

Furthermore, the information related to the growth degree of the fruit 101 of the agricultural crop 100 obtained by the sensing system 1 of the present invention and stored in the database 36 can be used for various applications as described in the section of the background art and is useful for activities of the agricultural operator.

Second Embodiment

Figure 9:
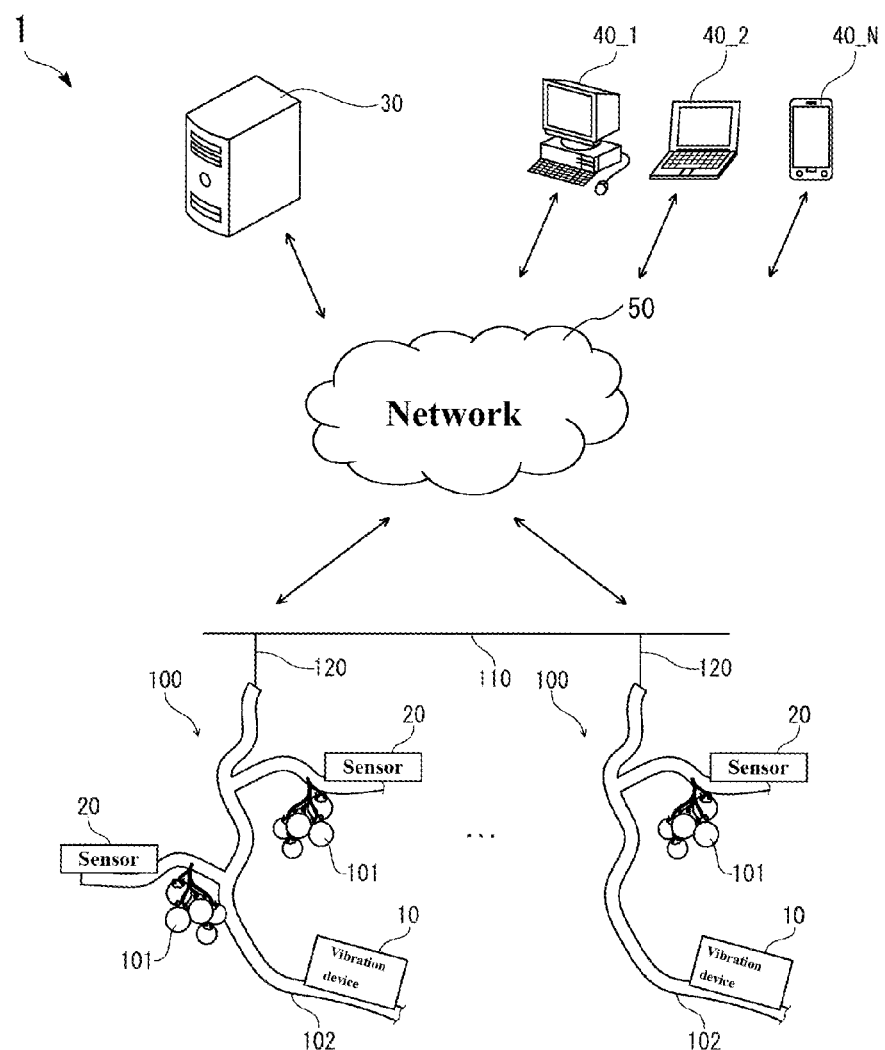
FIG. 9 is a conceptual diagram showing an embodiment of a sensing system according to a second embodiment of the present invention.

Next, a sensing system according to a second embodiment of the present invention will be described with reference to FIG. 9. FIG. 9 is a conceptual diagram showing an embodiment of a sensing system according to the second embodiment of the present invention. Hereinafter, the sensing system of the second embodiment will be described by placing emphasis on the points differing from the sensing system of the first embodiment with the same matters being omitted from the description.

The sensing system 1 of the second embodiment has the same configuration as that of the sensing system 1 of the first embodiment except that the computing device 30, the vibration device 10, the sensor 20 and the user device 40 can communicate with each other through a network 50.

The network 50 may be a wide range of networks containing an intranet, a local area network (LAN), a wide area network (WAN), the Internet and a combination thereof. The network 50 may be a private network or a shared network. The shared network is a connection among various types of networks and enables communication with each other by using various protocols (e.g., HTTP, TCP/IP, WAP). In addition, the network 50 may contain a variety of network devices such as a router, a bridge, a server, a computing device, a storage device and the like.

In the present embodiment, the communication between the computing device 30 and the vibration device 10 or the sensor 20 and the communication between the computing device 30 and the user device 40 are performed through the network 50. Therefore, in the present embodiment, there is no need to arrange the computing device 30, the vibration device 10, the sensor 20 and the user device 40 so as to be close to each other.

Therefore, the sensing system 1 of the present embodiment can be used for large-scale agriculture in which a lot of agricultural crops 100 are cultivated in a wide area. By using the sensing system 1 of the present embodiment, it is possible to know the growth degrees of the fruits 101 of the agricultural crops 100 cultivated in the wide area in an integrated manner and thus it is possible to promote increase in scale and efficiency of the agriculture.

Further, in the sensing system 1 of the present embodiment, the plurality of agricultural crops 100 to which the vibration devices 10 and the sensors 20 are respectively attached may be cultivated in different vinyl houses. By using the sensing system 1 of the present embodiment in this manner, the growth environments of the agricultural crops 100 in the different vinyl houses can be different from each other and data for investigating which environment is most effective for the growth of the fruit 101 of the agricultural crop 100 can be easily collected.

Although the above description has been provided as the computing device 30 is implemented as a single device as shown in FIG. 2, the present invention is not limited thereto. For example, the computing device 30 may be implemented within each user device 40.

Further, although the memory 33 and the database 36 are provided in the computing device 30 on which the processor 31 is mounted in each embodiment, the present invention is not limited thereto. For example, each of the memory 33 and the database 36 may be a remote storage device provided outside the computing device 30 so that each of the memory 33 and the database 36 can communicate with the processor 31.

Furthermore, in another embodiment, the present invention is a computer readable medium (i.e., the memory 33) storing computer readable instructions (i.e., the modules 34) thereon. The computer readable instructions contain computer-readable instructions (i.e., the communication module 341, the resonance frequency identifying module 342, the growth degree determining module 343, and the other module 344) for performing the particular tasks or the particular functions.

Figure 10:
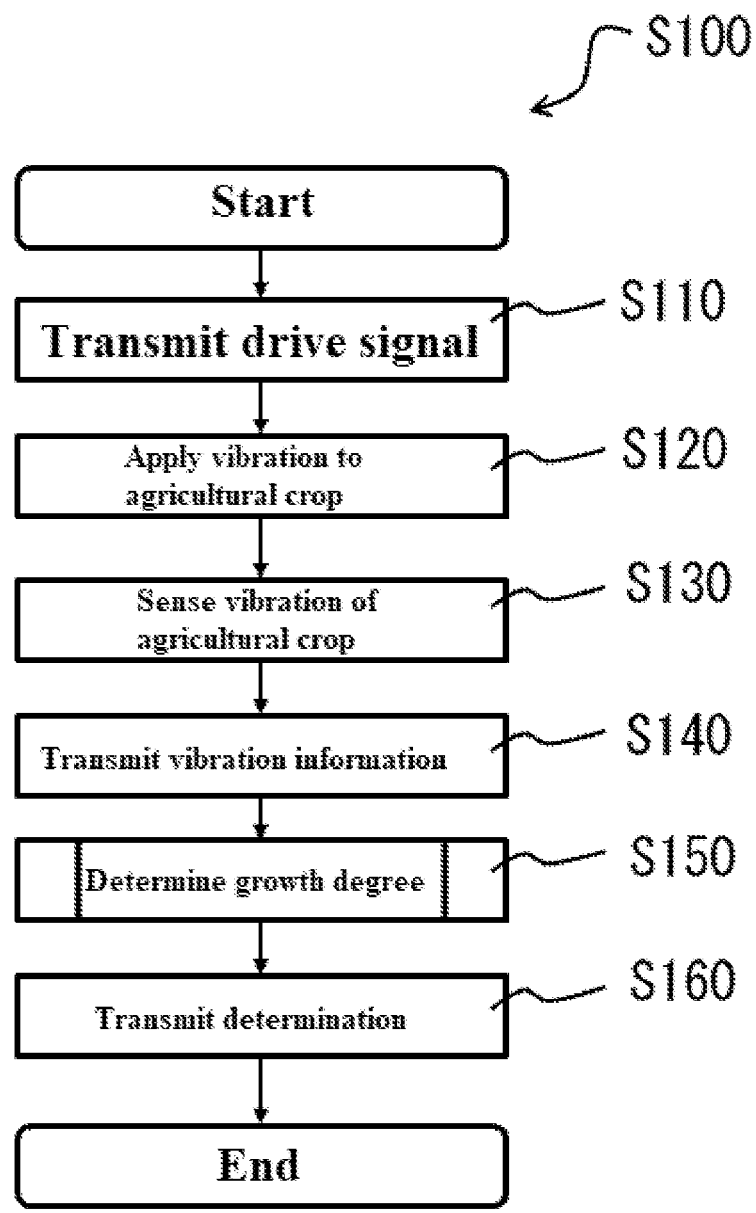
FIG. 10 is a flowchart for explaining a sensing method of the present invention.
Figure 11:
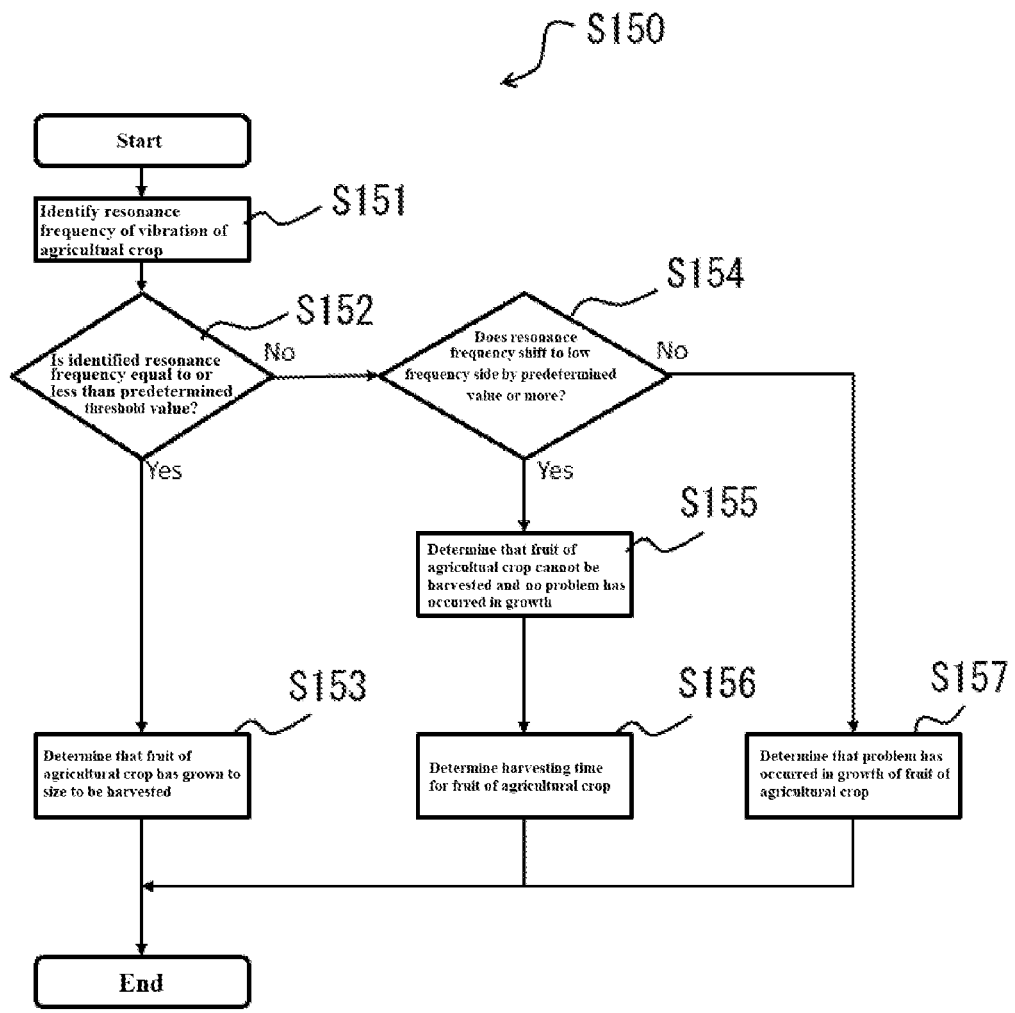
FIG. 11 is a flowchart for explaining a step for determining a growth degree of the agricultural crop shown in FIG. 10 in more detail.

Next, a sensing method of the present invention will be described with reference to FIG. 10. FIG. 10 is a flowchart for explaining the sensing method of the present invention. FIG. 11 is a flowchart for explaining a step for determining the growth degree of the agricultural crop shown in FIG. 10 in more detail.

Although the sensing method of the present invention can be performed by using the sensing system 1 of the present invention described above and any system having the same function as that of the sensing system 1 of the present invention, the following description will be given with assuming that the sensing method is performed by using the sensing system 1.

A sensing method S100 of the present invention is started when the drive signals are transmitted from the computing device 30 to the vibration device 10 and the sensor 20 at the predetermined cycle or any timing. At a step S110, the computing device 30 refers to the sensor-related data 361 in the database 36 and determines which sensors 20 and the corresponding vibration device 10 should be driven. Next, the computing device 30 uses the communication module 341 to transmit the drive signals to the sensor 20 and the corresponding vibration device 10 to be driven for driving the vibration device 10 to apply the vibration to the agricultural crop 100 and driving the sensor 20 to sense the vibration of the agricultural crop 100 caused by the vibration applied from the vibration device 10 to the agricultural crop 100.

At a step S120, the vibration device 10 which receives the drive signal from the computing device 30 is driven to apply the vibration to the agricultural crop 100 to which the vibration device 10 is attached. At a step S130, the sensor 20 senses the vibration of the agricultural crop 100 caused by the vibration applied from the vibration device 10. At a step S140, the sensor 20 transmits the vibration information related to the vibration of the agricultural crop 100 to the computing device 30 together with the sensor identification information for identifying the sensor 20 and any other information.

At a step S150, the computing device 30 identifies one local maximum value among the plurality of local maximum values in the frequency spectrum obtained from the vibration information received from the sensor 20 as the resonance frequency f of the vibration of the agricultural crop 100 to determine the growth degree of the fruit 101 of the agricultural crop 100 based on the identified resonance frequency f. At this time, the computing device 30 associates the vibration information received from the sensor 20 with the sensor identification information for identifying the sensor 20 or any other information and adds the vibration information received from the sensor 20 to the vibration information accumulation data 363 in the database 36.

FIG. 11 shows a detailed flow chart of the step S150. At a step S151, the computing device 30 uses the resonance frequency identifying module 342 to identify one local maximum value among the plurality of maximum values in the frequency spectrum obtained from the received vibration information related to the vibration of the agricultural crop 100 as the resonance frequency f of the vibration of the agricultural crop 100. At a step S152, the computing device 30 uses the growth degree determining module 343 to compare the resonance frequency f of the vibrations of the agricultural crop 100 identified in the step S151 with the predetermined threshold value contained in the growth determination information 362 in the database 36. When the resonance frequency f of the vibration of the agricultural crop 100 is equal to or lower than the predetermined threshold, the process of the step S150 shifts to a step S153. At the step S153, the computing device 30 determines that the fruit 101 of the agricultural crop 100 has grown to the size to be harvested and then the process of the step S150 ends.

On the other hand, in the case of determining that that the resonance frequency f of the vibration of the agricultural crop 100 is larger than the predetermined threshold value at the process S152, the process of the step S150 shifts to a step S154. At the step S154, the computing device 30 uses the resonance frequency identifying module 342 to identify one local maximum value among the plurality of local maximum values in the frequency spectrum obtained from the vibration information of the vibration of the agricultural crop 100 obtained by the previous measurement as the resonance frequency f of the vibration of the agricultural crop 100 of the previous measurement. Next, the computing device 30 uses the growth degree determining module 343 to compare the resonance frequency f of the vibration of the agricultural crop 100 of the previous measurement with the resonance frequency f of the vibration of the agricultural crop 100 identified from the vibration information obtained in the current measurement. Here, it is determined whether or not the resonance frequency f of the vibration of the agricultural crop 100 shifts to the low frequency side by the predetermined value or more which is contained in one information constituting the growth determination information 362 in the database 36.

If the resonance frequency f of the vibration of the agricultural crop 100 shifts to the low frequency side by the predetermined value or more, the process of the step S150 shift to a step S155. At the step S155, the computing device 30 determines that the fruit 101 of the agricultural crop 100 has not grown to the size to be harvested but no problem has occurred in the growth of the fruit 101. After that, at a step S156, the computing device 30 uses the growth degree determining module 343 to determine the harvesting time for the fruit 101 by referring to the table or the mathematical equation for determining the harvesting time for the fruit 101 from the difference between the calculated resonance frequency f of the vibration of the agricultural crop 100 stored as the growth determination information 362 in the database 36 and the predetermined threshold value and/or the change amount Δf of the resonance frequency f of the vibration of the agricultural crop 100. Next, the process of the step S150 ends.

On the other hand, in the case of determining that the resonance frequency f of the vibration of the agricultural crop 100 does not shift to the low frequency side by the predetermined value or more at the step S154, the process of the step S150 shifts to a step S157. In the step S157, the computing device 30 determines that a problem has occurred in the growth of the fruit 101 of the agricultural crop 100. Next, the process of the step S150 ends.

Returning back to FIG. 10, at a step S160, the computing device 30 uses the communication module 341 to transmit the determination obtained at the step S150 to the user device 40 and then the sensing method S100 ends. The user can know the growth degree of the fruit 101 of the agricultural crop 100 by referring to the determination transmitted from the computing device 30 to the user device 40.

Although the sensing system 1, the sensing method S100 and the non-transitory computer readable medium according to the present invention have been described above with reference to the illustrated embodiments, the present invention is not limited thereto. Each configuration of the present invention can be replaced with any configuration capable of performing the same function or any configuration can be added to each configuration of the present invention.

For example, the number and types of the components of the sensing system 1 shown in FIG. 2 and the computing device 30 shown in FIG. 8 are merely illustrative examples and the present invention is not necessarily limited thereto. An aspect in which any component is added or combined or any component is omitted without departing from the principle and intent of the present invention is also involved within the scope of the present invention. Further, each component of the sensing system 1 may be practiced by a hardware, a software or a combination thereof. In particular, although the modules 34 have been described as being implemented as a software performed according to the computer readable instructions stored in the memory 33, an aspect that the functionality of each module 34 is implemented by a hardware is also involved in the present invention. Furthermore, the modules 34 may be implemented as software modules executed in a cloud-based computing environment on any network.

In addition, the numbers and types of the steps of the sensing method S100 shown in FIGS. 10 and 11 are merely illustrative examples and the present invention is not necessarily limited thereto. An aspect that any steps have been added or combined for any purpose or any steps have been omitted without departing from the principles and intent of the present invention is also involved within the scope of the present invention.

INDUSTRIAL APPLICABILITY

The sensing system of the present invention uses the vibration device to apply the vibration to the agricultural crop, identifies one local maximum value among the plurality of local maximum values contained in the frequency spectrum obtained from vibration information related to the vibration of the agricultural crop caused by the applied vibration and senses the growth degree of the fruit of the agricultural crop based on the identified resonance frequency. When the agricultural crop is vibrated, the vibrating agricultural crop can be considered as the resonant system defined by the spring constant of the stem of the agricultural crop, the mass of the agricultural crop and the masses of the vibration device and the sensor. The resonance frequency of such a resonance system is not affected by the disturbances such as the changes in the surrounding environment of the agricultural crop (e.g., blowing wind or rain against the fruit of the agricultural crop). Therefore, by sensing the growth degree of the fruit of the agricultural crop based on the resonance frequency of the vibration of the agricultural crop, it is possible to sense the growth degree of the fruit of the agricultural crop more accurately than the method of directly measuring the mass of the fruit of the agricultural crop which is likely to be affected by the disturbances.

Further, when the agricultural crop is vibrated, the frequency spectrum obtained from the vibration information related to the vibration of the agricultural crop may contain the plurality of local maximum values caused by the factors (such as the mass of the wire for training the agricultural crop and the masses of the vibration device and the sensor attached to the stem of the agricultural crop) other than the mass of the fruit of the agricultural crop in addition to the local maximum value (the resonance frequency) caused by the mass of the fruit of the agricultural crop. In the sensing system of the present invention, one local maximum value among the plurality of local maximum values contained in the frequency spectrum obtained from the vibration information related to the vibration of the agricultural crop is identified as the resonance frequency of the vibration of the agricultural crop. Therefore, it is possible to perform only the measurement for the fruit of the agricultural crop which should be measured and exclude the local maximum values (the resonance frequencies) caused by the factors other than the mass of the fruit of the agricultural crop from the measurement target. Thus, the present invention has industrial applicability.

The invention claimed is:

1. A sensing system for sensing an increase in mass of a fruit of an agricultural crop, comprising:
   at least one vibration device attached to a stem of the agricultural crop for applying vibration to the agricultural crop;
   at least one sensor attached to the stem of the agricultural crop for sensing vibration of the agricultural crop caused by the vibration applied to the agricultural crop from the vibration device to transmit vibration information related to the vibration of the agricultural crop; and
   a computing device for identifying one local maximum value among a plurality of local maximum values in a frequency spectrum obtained from the vibration information received from the at least one sensor as a resonance frequency of the vibration of the agricultural crop to determine the increase in the mass of the fruit of the agricultural crop based on the identified resonance frequency,
   wherein the vibration device includes a case configured to be attachable to the stem of the agricultural crop, a coil fixedly provided on a bottom surface of the case, a leaf spring provided so as to be capable of vibrating with respect to the case, and a magnet assembly attached to the leaf spring so as to be spaced apart from the coil, and
   wherein the fruit of the agricultural crop fruits at a point located between a point of the stem of the agricultural crop to which the at least one sensor is attached and a point to which the at least one vibration device is attached.

2. The sensing system as claimed in claim 1, wherein determination for the increase in the mass of the fruit of the agricultural crop contains determination for a harvest time for the fruit of the agricultural crop.

3. The sensing system as claimed in claim 1, wherein the computing device determines that the fruit of the agricultural crop has grown to a size to be harvested when the identified resonance frequency is equal to or less than a predetermined threshold value.

4. The sensing system as claimed in claim 1, wherein the sensing system uses the vibration device, the sensor and the computing device to identify the resonance frequency of the vibration of the agricultural crop at a predetermined cycle, and
   wherein the computing device compares the resonance frequency of the vibration of the agricultural crop identified from the vibration information obtained in a previous measurement with the resonance frequency of the vibration of the agricultural crop identified from the vibration information obtained in a current measurement and determines that a problem has occurred in a growth of the fruit of the agricultural crop when the resonance frequency of the vibration of the agricultural crop does not shift to a low frequency side by a predetermined value or more.

5. The sensing system as claimed in claim 1, wherein the computing device transmits determination for a growth of the agricultural crop to a user device.

6. The sensing system as claimed in claim 1, wherein the agricultural crop is selected from the group consisting of tomato, eggplant, cucumber, pepper, and strawberry.

7. The sensing system as claimed in claim 1, wherein the resonance frequency of the agricultural crop is identified based on prediction from prior information that can be obtained in advance, and
wherein the prior information contains a predicted mass of the fruit of the agricultural crop, a type of the agricultural crop, or a period from planting the agricultural crop.

8. The sensing system as claimed in claim 1, wherein the resonance frequency the agricultural crop is identified based on a shift amount of each of the local maximum values.

9. The sensing system as claimed in claim 1, wherein the vibration device and the sensor are arranged so as to be spaced apart from each other by at least 10 to 20 cm.

10. The sensing system as claimed in claim 1, wherein the case contains the coil, the leaf spring and the magnet assembly therein, and
wherein the case is a cylindrical member including a cover, a base and a cylindrical portion located between the cover and the base.

11. The sensing system as claimed in claim 10, wherein the leaf spring has a ring shape with an outer peripheral portion held between the base and the cylindrical portion of the case, and a central portion containing a central opening portion,
wherein the magnet assembly is attached to the central portion, and
wherein the central portion can vibrate with respect to the base so that the magnet assembly can vibrate with respect to the coil.

12. A sensing method performed by a sensing system containing a computing device including a processor for sensing an increase in mass of a fruit of an agricultural crop, comprising:
transmitting, by the processor, drive signals to at least one vibration device and at least one sensor each attached to a stem of the agricultural crop for driving the at least one vibration device to apply vibration to the agricultural crop and driving the at least one sensor to sense vibration of the agricultural crop caused by the vibration applied to the agricultural crop from the at least one vibration device;
receiving, by the processor, vibration information related to the vibration of the agricultural crop from the at least one sensor;
identifying, by the processor, one local maximum value among a plurality of local maximum values in a frequency spectrum obtained from the vibration information received from the at least one sensor as a resonance frequency of the vibration of the agricultural crop; and
determining, by the processor, the increase in the mass of the fruit of the agricultural crop based on the identified resonance frequency,
wherein the vibration device includes a case configured to be attachable to the stem of the agricultural crop, a coil fixedly provided on a bottom surface of the case, a leaf spring provided so as to be capable of vibrating with respect to the case, and a magnet assembly attached to the leaf spring so as to be spaced apart from the coil, and
wherein the fruit of the agricultural crop fruits at a point located between a point of the stem of the agricultural crop to which the at least one sensor is attached and a point to which the at least one vibration device is attached.

13. A non-transitory computer readable medium storing computer readable instructions executed by a computing device including a processor for sensing an increase in mass of a fruit of an agricultural crop, wherein the computer readable instructions comprise:
an instruction for transmitting drive signals to at least one vibration device and at least one sensor each attached to a stem of the agricultural crop for driving the at least one vibration device to apply vibration to the agricultural crop and driving the at least one sensor to sense vibration of the agricultural crop caused by the vibration applied to the agricultural crop from the at least one vibration device;
an instruction for receiving vibration information related to the vibration of the agricultural crop from the at least one sensor;
an instruction for identifying one local maximum value among a plurality of local maximum values in a frequency spectrum obtained from the vibration information received from the at least one sensor as a resonance frequency of the vibration of the agricultural crop; and
an instruction for determining the increase in the mass of the fruit of the agricultural crop based on the identified resonance frequency,
wherein the vibration device includes a case configured to be attachable to the stem of the agricultural crop, a coil fixedly provided on a bottom surface of the case, a leaf spring provided so as to be capable of vibrating with respect to the case, and a magnet assembly attached to the leaf spring so as to be spaced apart from the coil, and
wherein the fruit of the agricultural crop fruits at a point located between a point of the stem of the agricultural crop to which the at least one sensor is attached and a point to which the at least one vibration device is attached.

* * * * *